(12) United States Patent
Denoel et al.

(10) Patent No.: US 9,314,518 B2
(45) Date of Patent: Apr. 19, 2016

(54) TREATMENT OF STREPTOCOCCAL INFECTIONS

(71) Applicant: GLAXOSMITHKLINE BIOLOGICALS S.A., Rixensart (BE)

(72) Inventors: Philippe Denoel, Rixensart (BE); Philippe Vincent Hermand, Rixensart (BE); Steve Labbe, Laval (CA); Jan Poolman, Haarlem (NL); Stephane Rioux, Rixensart (BE)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 14/176,199

(22) Filed: Feb. 10, 2014

(65) Prior Publication Data

US 2014/0205634 A1    Jul. 24, 2014

Related U.S. Application Data

(62) Division of application No. 13/581,940, filed as application No. PCT/EP2011/053485 on Mar. 8, 2011, now abandoned.

(30) Foreign Application Priority Data

Mar. 9, 2010 (GB) .................................. 1003920.4

(51) Int. Cl.
*A61K 39/09* (2006.01)
*A61K 39/00* (2006.01)

(52) U.S. Cl.
CPC ..... *A61K 39/092* (2013.01); *A61K 2039/55505* (2013.01); *A61K 2039/55566* (2013.01); *A61K 2039/55572* (2013.01)

(58) Field of Classification Search
None
See application file for complete search history.

(56) References Cited

FOREIGN PATENT DOCUMENTS

| WO | 00/37105 | 6/2000 |
|---|---|---|
| WO | 00/39299 | 7/2000 |
| WO | 01/14421 | 3/2001 |
| WO | 01/98334 | 12/2001 |
| WO | 02/22167 | 3/2002 |
| WO | 02/22168 | 3/2002 |
| WO | 03/054007 | 7/2003 |
| WO | 2009/012588 | 1/2009 |

OTHER PUBLICATIONS

Loisel, et al., AdcAII, A New Pneumococcal Zn-Binding Protein Homologous with ABC Transporters: Biochemical and Structural Analysis, J Mol Biol 381(3): 594-606 (2008).
Ogunniyi et al, Pneumococcal histidine triad proteins are regulated by the Zn2+-dependent repressor AdcR and inhibit complement deposition through the recruitment of complement factor H, FASEB Journal 23(3): 731-738 (2009).
International Search Report for priority application PCT/EP2011/053485.
Panina EM, Mironov AA, Gelfand MS. Comparative genomics of bacterial zinc regulons: Enhanced ion transport, pathogenesis, and rearrangement of ribosomal proteins. Proc. Natl. Acad. Sci. 100(17), 9912-9917 (2003).
Adamou, et al. Identification and Characterization of a Novel Family of Pneumococcal Proteins That are Protective against Sepsis. Infection & Immunity 69:949-968 (2001).
Kumar, et al. Blood Zinc Levels in Children Hospitalized with Severe Pneumonia: A Case Control Study. Indian Pediatrics 4: 483-491 (2004).
McBean, et al. Zinc concentration in human tissues. AJCN 25:672-676 (1972).
Strand, et al. Pneumococcal pulmonary infection, septicaemia and survival in young zinc-depleted mice. British J. Nutrition 86:301-306 (2001).
Bargagli et al. Analysis of Trace Elements in Bronchoalveolar Lavage of Patients with Diffuse Lung Diseases. Biol Trace Elem Res (2008) 124:225-235.
Sullivan et al. Serum Levels of Selenium, Calcium, Copper Magnesium, Manganese and Zinc in Various Human Diseases. J Nutr (1979) 109:1432-1437.
Vallee and Gibson. The Zinc Content of Normal Human Whole Blood, Plasma, Leucocytes, and Erythrocytes. J Biol Chem (1948) 176:445-457.
Buxaderas and Farre-Rovira. Whole Blood and Serum Zinc Levels in Relation to Sex and Age. Revista Expanola de Fisiologia (1985) 41:463-470.

*Primary Examiner* — Jennifer Graser
(74) *Attorney, Agent, or Firm* — Alice P. Bradney

(57) ABSTRACT

Methods of treating a *Streptococcus pneumoniae* infection are described herein.

3 Claims, 21 Drawing Sheets

(a)  SEQ ID NO:1

Figure 1:
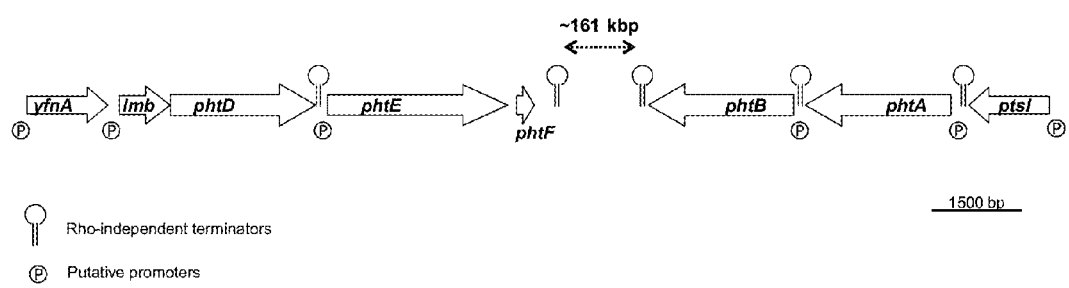

```
                                    -35                        -10
5131 TCTTTTTTAGAAAAACGTAACAGAAACTTGACAAAAGTAATTTTAAATAGTAAACTATTT
        +1
5191 ACTGGTTAATTAAATGGTTAAATAACCGGTTTAGAAAACTATTTAATAAAGTAAAAGAAG
                                       rbs      phtE ———▶
5251 TTGAGAAAAAACTTCATCATTTATTGAAATGAGGGATTTATGAAATTTAGTAAAAAATAT
```

(b)  SEQ ID NO:2

```
                 -35                   -10       +1
2341 AAAATTCTTGACAAGTTGGATATTTAGGAGTAAACTATTAACCAGTTAAGTAATAGAGAG
                                                      rbs
2401 GAGTTTCTGCAATTTAGAAATGAATTGCAACTAGAAATATCAAATAGAAAGAGAGTTTCG
        phtA    ———▶
2461 ATGAAAATTAATAAGAAATACCTTGTTGGTTCTGCGGCAGCTTTGATTTT
```

(c)  SEQ ID NO:3

```
          -35                 -10        +1
4969 TTCTTGACAAGCAATATTAAAAGAGTAAACTATTAACTAGTTAATTAACCGGTTTATTA
                                     rbs       phtB ———▶
5029 CTTTATAGTGAATCAAATATACTTAAGAAAAGAGGAAAGAATGAAAATTAATAAAAAATA
```

(d)  SEQ ID NO:4

```
                  -35              -10           +1
1561 CTAAAAATATCTTGACAGATTAAATTTTCAGGAGTAGAATATTTACTAGTTAATTAAAG
        rbs      lmb ———▶
1621 GTTAAGGAGTTGTTCATGAAGAAACAAAATTTATTTTTAGTCCTGTTAA
```

(e)  SEQ ID NO:5

```
                 -35                     -10       +1
   1 GTTACGGTAGTCAGATTTTTTTAGAAAAACATTTTATAAATATTCACATATCTCCTATAT
                                   rbs       yfnA ———▶
  61 TTATGGTAAAATAGAATTATCAGTTTATTTTGGAGTCAAAGATGAATATATTTAGAACAA
```

Figure 2.

(a)
```
                SEQ ID NO:6                    SEQ ID NO:7
      ·······▶ phtE            8420     8631 phtF  ──────▶
 8391 ATCTGATCTCATAGCGTAAGGAATAGCAGT... AATTATGAAATTTAAAAAGAAATATATAGC

8661 AGCTGGATCTGTTGTTATCCTTTCCTTAAGTCTGTGTGTTTATGCTCTGAACCAACATAG

8721 CTAACAGGCCAATACAGATAAAAATCGTGTTTCATATGTAAACAGTAATAAAGACACTAA
                                           8810    8990   SEQ ID NO:8
 8781 GAAGACTGAAAATTTGACTCCAGACTAGGT...TCAGTTAGGTTAAGGGAGGATATATTATTAA

9021 GGTAGATGGAAAGTATTATGTTTACCTTAAAGATCAAGCTCATGCAGAAAATGTACGAAC
                                             9120   10261  SEQ ID NO:9
 9081 AAAAGATGAAATCAATCGCCAAAAACAAGAACATGGTAAA...TAGCGCCCTTCAACAAGAAA

10281 AGGAAAATGCTGAGCAAGATCCTCAGACACTTGTACTCTATCAAAAACTC
```

(b)
```
      SEQ ID NO:10
      ·······▶ phtB
 7511 AAACTATTGGCTTTATTAAAGGAGAGTAAGTAAAGGTAGCAGCATTTTCTAACTCCTAA

7571 AACAGGATAGGAGAACGGGAAAACGAAAAATGAGAGCAGAATGTGAGTTCTAGTTCTCA

7631 TTTTTTTCATGAAAT
```

```
      SEQ ID NO:11
(c)
      ·······▶ phtD
 5051 AAAGAAAGTCAACCGGCTCCTATACAGTAGTAAAATGAATGGAGCATATTTTATGGAGAA

5111 GTAACCTTTCGTGTTACTTCTCTTTTTTAGAAAAACGTAACAGAAACTTGACA
```

(d)
```
      SEQ ID NO:12
      ·······▶ phtA
 4891 AGTAAGGAAAAAATAAACTAATGAAAAATGAAAGTCTCGATAAAGAGGCTTTCATTTTTA

4951 TTATGTATATATGTAAAATTCTTGACAAGCAATATTAAAAAGAG
```

(e)
```
      SEQ ID NO:13
      ·······▶ ptsI
 2191 ACGTTAATTTTGATTAATCGAAAAGTCCCTGCAACTCAGTTACAGGGATTTTTTTGATAT

2251 TTTAAA
```

Figure 3.

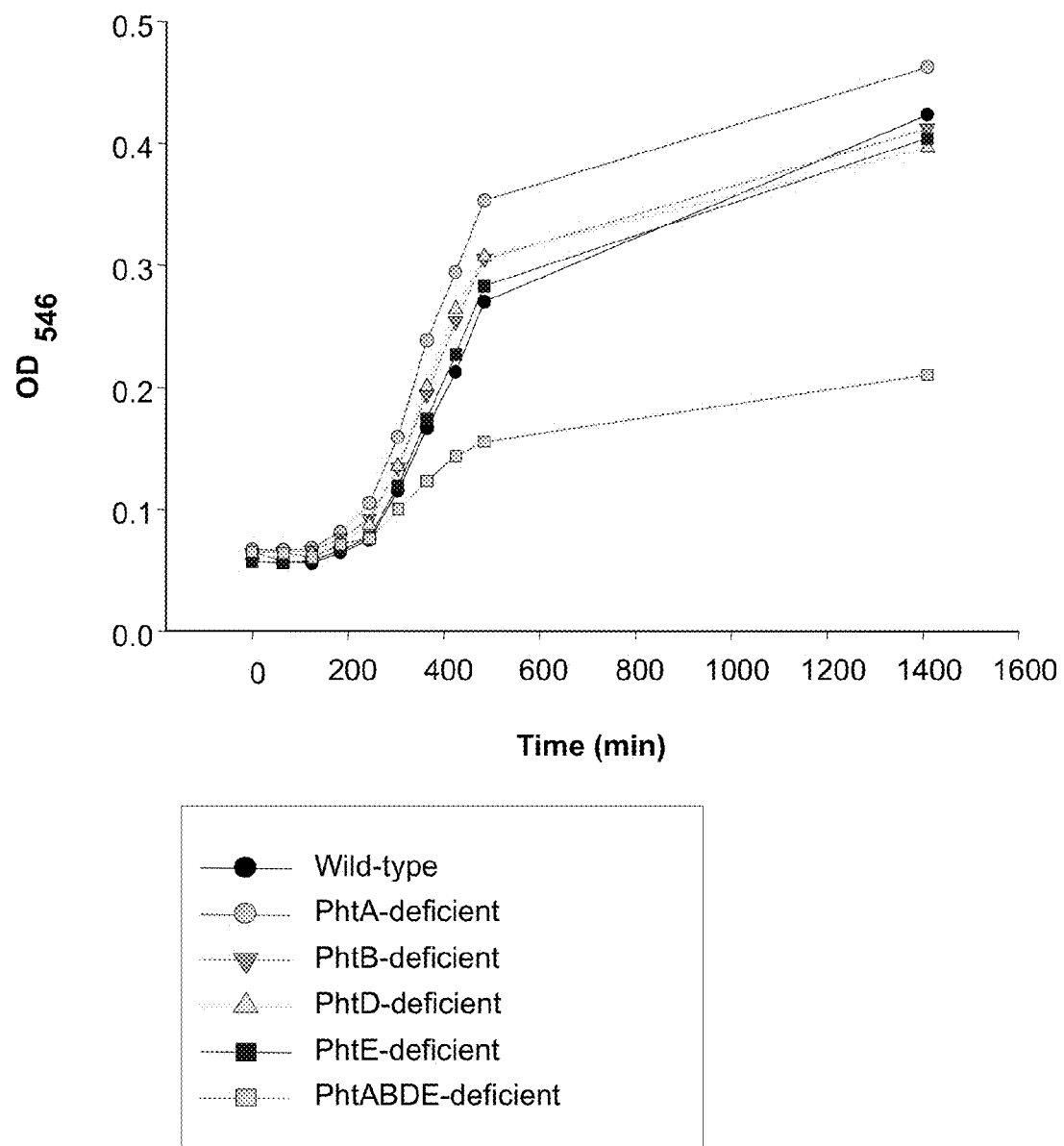

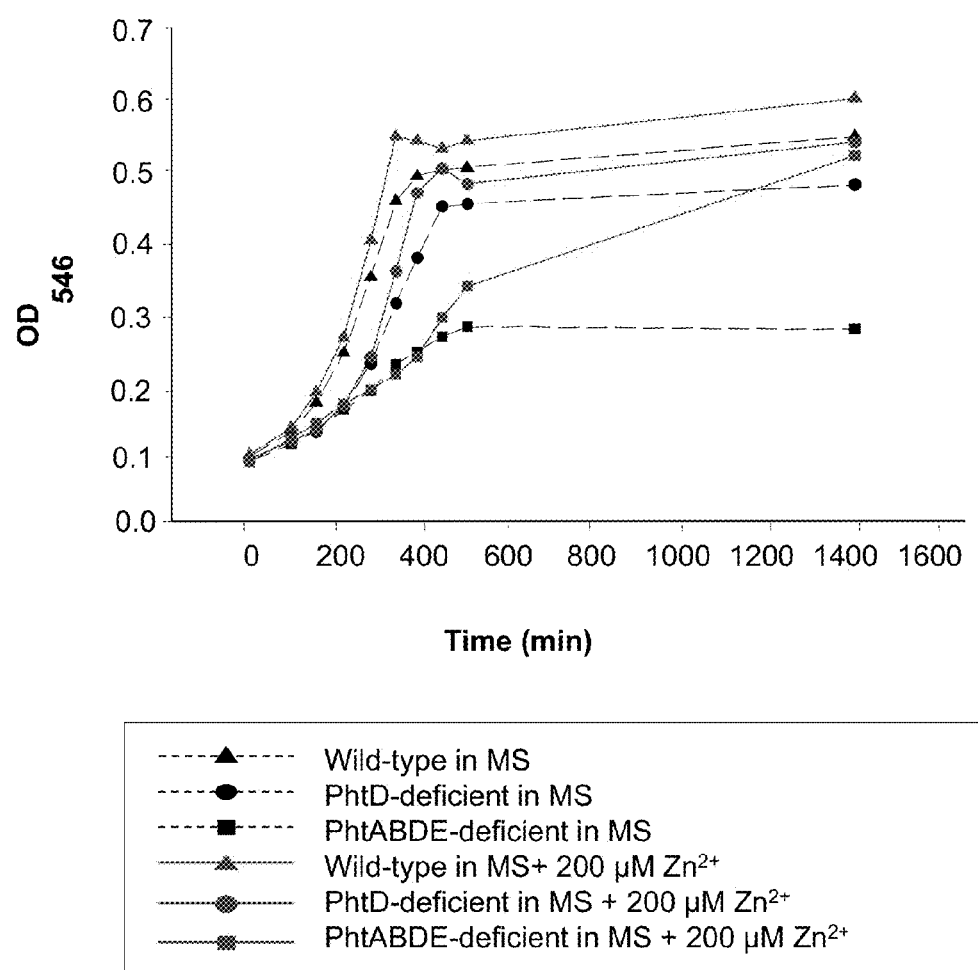

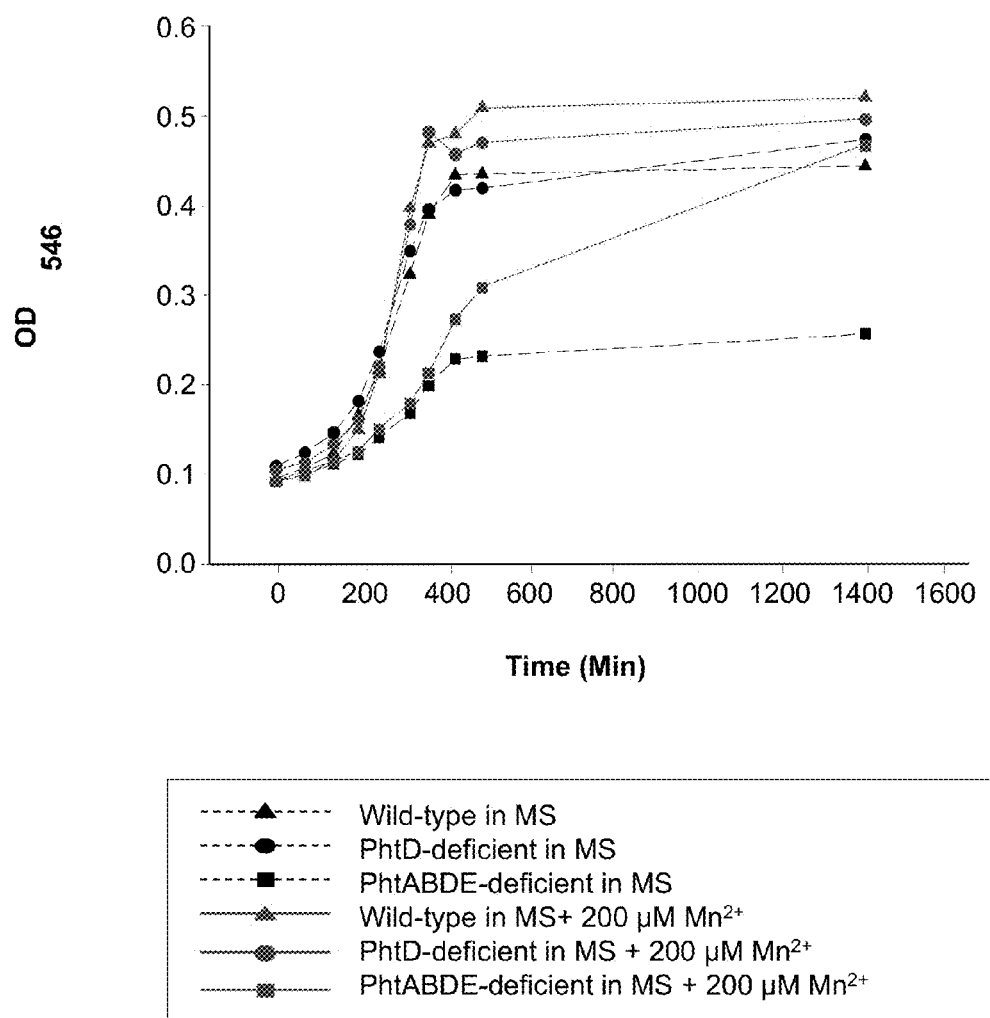

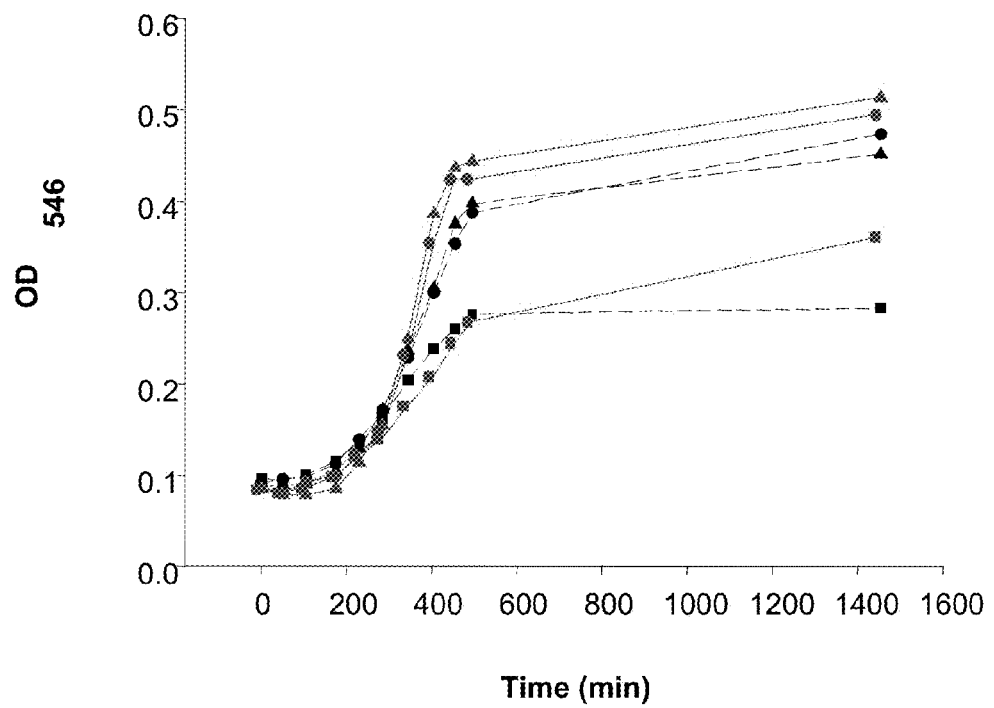
Growth curves in MS + $Fe^{2+}$
Figure 6d
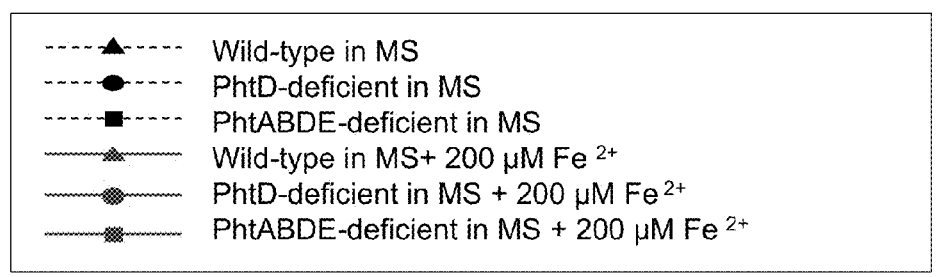

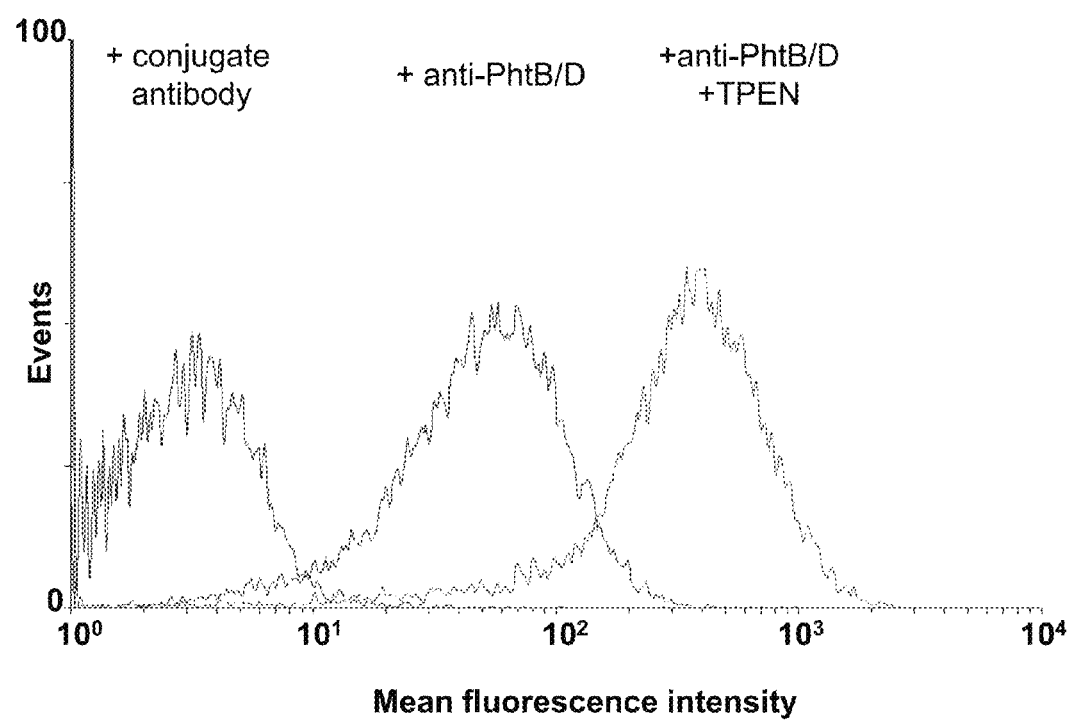

| Signal sequence for | Number of sequence analysed | Signal sequence | | | | | | |
|---|---|---|---|---|---|---|---|---|
| Signal sequence for PhtA | 7 | | V | - | A | A | I | | SEQ ID NO:14 |
| Signal sequence for PhtB | 8 | | | | V | T/V | V | | SEQ ID NO:15-16 |
| Signal sequence for PhtD | 72 | | | - | V | V | A | | SEQ ID NO:17-18 |
| Signal sequence for PhtE | 8 | F S | I | A G | A V | I | V S | L | SEQ ID NO:19 |

Figure 9.

TREATMENT OF STREPTOCOCCAL INFECTIONS

This application is a divisional application of U.S. application Ser. No. 13/581,940 filed Aug. 30, 2012, currently pending, which was filed pursuant to 35 U.S.C. §371 as a United States National Phase Application of International Patent Application Serial No. PCT/EP2011/053485 filed Mar. 8, 2011, which claims priority to United Kingdom Application No. 1003920.4 filed Mar. 9, 2010; the contents of each of the foregoing applications are hereby incorporated by reference.

The present application relates to the field of vaccines and immunogenic compositions that protect against Streptococcal disease and particularly to methods of treating *Streptococcus pneumoniae* disease using vaccines containing proteins from the polyhistidine triad family of proteins, and in particular, to methods of treatment using these vaccines and immunogenic compositions

BACKGROUND

*Streptococcus pneumoniae* is one of the leading causes of infectious morbidity and mortality in the world, responsible for a large spectrum of infections such as otitis media, pneumonia, bacteremia and meningitis {Hausdorff 2005, McCullers 2001}. The emergence of antibiotic-resistant strains of this micro-organism has further underlined the need for providing effective prophylactic vaccination {Lynch, III 2005, Bridy-Pappas 2005}.

Current vaccines are composed of epidemiologically dominant serotype-based selections of pneumococcal capsular polysaccharides, conjugated or not to a carrier protein {Dagan 2004, Fedson 2004, Mbelle 1999, Smart 1987}. However, the vaccine formulations do not cover all serotypes of this micro-organism, which might particularly be of relevance in certain regions of the globe with different dominant serotypes {Dagan 1992}. In addition, one may expect that the use of serotype-specific vaccines could allow at term the positive selection of non-vaccine serotypes {Nunes 2008, Singleton 2007}.

An alternative approach involves the development of vaccines that target common pneumococcal antigens. Among multiple candidates, the Pht protein family, restricted to the genus *Streptococcus*, comprises promising ones, being well-conserved across the pneumococcal species {Hamel 2004, Zhang 2001}, and being antibody targets in infected individuals and protective upon challenge in immunized mice {Beghetto 2006}. Originally, this protein family was independently reported by three groups, and three separate denominations were used: Pht (for pneumococcal histidine triad) {Adamou 2001}, Php (for pneumococcal histidine protein) {Zhang 2001}, and BVH {Hamel 2004}. Those proteins are characterized by a histidine triad motif, HxxHxH, repeated five to six times in their amino-acid sequences. Four members of this family have been described: PhtA (BVH-11-3), PhtB (PhpA/BVH-11) and PhtD (BVH-11-2) that share up to 81% sequence identity, and PhtE (BVH-3) that diverges from the three other proteins, showing only up to 35% identity with them. It is a longer protein, the only one with six repeats of the histidine triad motif. In mouse immunization studies, all members of the Pht family have been shown to afford a high level of protection to subsequent pneumococcal infection with a number of different strains/serotypes {Adamou 2001, Hamel 2004, Ogunniyi 2007, Wizemann 2001, Zhang 2001}.

Despite their potential importance in vaccination against *S. pneumoniae*, the biological function of these proteins has yet to be determined. Results from antibody-labeling and flow cytometry experiments demonstrated that the Pht proteins are exposed on the surface of the encapsulated bacterium {Hamel 2004}, which is in agreement with their relevance as vaccine target. By signature-tagged mutagenesis, it has been suggested that PhtA, PhtB, and PhtD are involved in lung-specific virulence {Hava 2002}, without further indication about their biological function. Among their putative roles, neutralization of the complement factor C3b has been suggested {Hostetter 1999, Ogunniyi 2009}, which implies that they would interfere with phagocytosis. Besides that, a role in adherence is also suspected. Indeed, a genetic link between phtD and lmb, the latter encoding a putative laminin adhesion protein {Spellerberg 1999}, has been reported {Panina 2003}. At last, due to the high number of histidine residues in the histidine triads, it has been suggested that the Pht proteins may be involved in DNA and/or metal binding {Adamou 2001}. More specifically, some studies highlighted a link between the Pht family and zinc. Indeed, AdcR-binding sites have been found in the upstream regions of the pht genes, AdcR being described as a transcription factor that regulates zinc uptake {Panina 2003}. Furthermore, the crystal structure of a portion of PhtA revealed the presence of zinc ions bound to a histidine triad domain {Riboldi-Tunnicliffe 2005}. It is not clear, however, whether zinc scavenging or transport is the function of those proteins, or whether zinc rather plays a conformational or functional role.

Important aspects that need to be addressed for vaccine candidates are their level of expression and associated regulation, their occurrence as well as their sequence variability. Therefore, we have addressed these different aspects with regard to the Pht proteins.

*Streptococcus pneumoniae* elicits different disease states exhibiting different pathologies depending on the site at which the pneumococcal population expands. Septicaemia occurs where the *S. pneumoniae* enters to blood steam, whereas pneumonia occurs where *S. pneumoniae* multiplies in the lung. *S. pneumoniae* is also an important pathogen in otitis media infections. *S. pneumoniae* can also enter the cerebrospinal fluid to cause meningitis.

There is a need to develop better pneumococcal vaccines which are able to target specific pneumococcal diseases and provide optimal protection against a particular form of pneumococcal disease.

Accordingly there is provided a method of treating or preventing *Streptococcus pneumoniae* infection wherein the *Streptococcus pneumoniae* infection occurs in an environment where the concentration of $Zn^{2+}$ and/or $Mn^{2+}$ is sufficiently low to upregulate the expression of at least one PhtX protein in the *Streptococcus pneumoniae*; comprising the step of administering a pharmaceutically effective amount of the PhtX protein to a human patient.

In a second aspect of the invention there is provided an immunogenic composition comprising a pharmaceutically effective amount of an isolated PhtX protein for use in the treatment or prevention of a *Streptococcus pneumoniae* infection wherein the *Streptococcus pneumoniae* infection occurs in a human patient in an environment where the concentration of $Zn^{2+}$ and/or $Mn^{2+}$ is sufficiently low to upregulate the expression of at least one PhtX protein in the *Streptococcus pneumoniae*.

In a third aspect of the invention there is provided a use of a pharmaceutically effective amount of an isolated PhtX protein in the manufacture of a medicament for the treatment or prevention of a *Streptococcus pneumoniae* infection wherein the *Streptococcus pneumoniae* infection occurs in a human patient in an environment where the concentration of $Zn^{2+}$ and/or $Mn^{2+}$ is sufficiently low to upregulate the expression of at least one PhtX protein in the *Streptococcus pneumoniae*.

FIGURE LEGENDS

FIG. 1. Organization of the pht genes in *Streptococcus pneumoniae* serotype 4 strain TIGR4.

FIG. 2. Promoter-containing upstream regions of the pht genes. (a) phtE gene, (b) phtA gene, (c) phtB gene, (d) lmb gene, (e) yfnA gene. The −35 and −10 regions are double-underlined, transcription start sites are indicated by a bold-face letter and the symbol (+1), putative ribosome binding sites (rbs) are underlined, and open reading frames are represented by arrows indicating the direction of transcription over a series of boldface letters. The numbers on the left correspond to sequence positions in GenBank accession numbers AY569979 (a, d and e) and AY569980 (b and c).

FIG. 3. Rho-independent transcription terminator sequences of the pht and ptsI genes. (a) phtE, (b) phtB, (c) phtD, (d) phtA and (e) pstI genes. Stop codons are underlined in boldface, terminator regions are underlined, and sequences underlined with a discontinuous line indicate the hairpin region of the terminators. Open reading frames are represented by arrows indicating the direction of transcription over a series of boldface letters. In (a), the region in italics (phtF gene; putative start codon doubly underlined) presents 78% identity with the first 481 bp of the phtE gene. However, underlined stop codons prevent significant gene translation. The numbers correspond to sequence positions in GenBank accession numbers AY569979 (a and c) and AY569980 (b, d and e).

Figure 4:
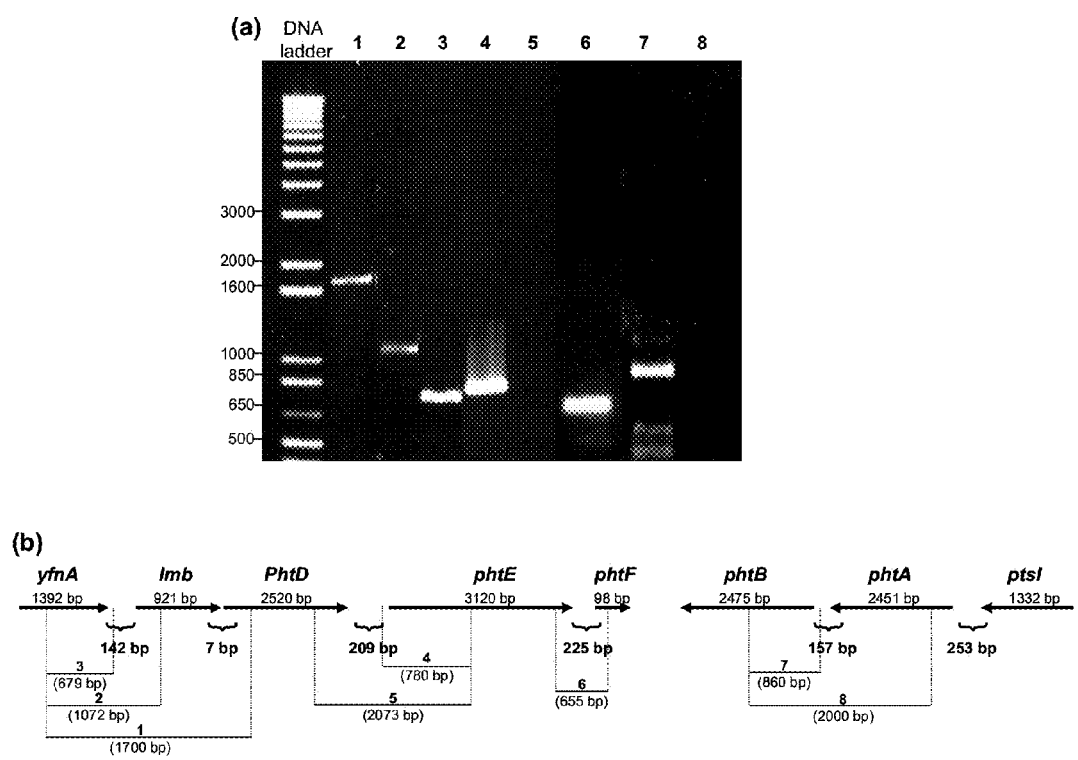

FIG. 4. RT-PCR analyses of the pht transcripts. (a) 1% agarose gel showing the RT-PCR products with template RNA from cells grown to mid-log growth phase. Lanes 1 to 8 correspond to regions 1 to 8 in the schematic representation in (b). The RT-PCR products shown in lanes 1 to 8 were generated using primer pairs that flanked the corresponding regions depicted in the scheme. The length of each predicted RT-PCR product is indicated in parentheses.

Figure 5:
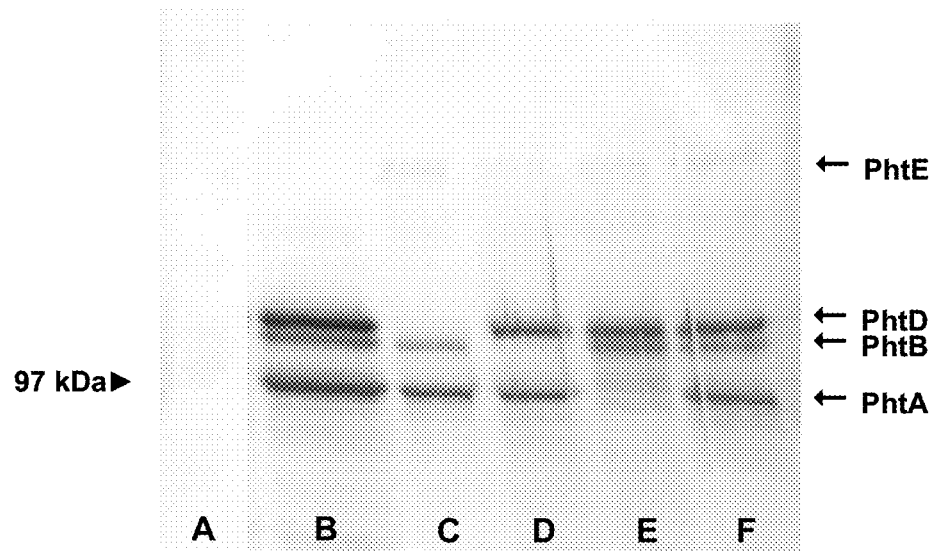

FIG. 5. SDS-PAGE immunoblotting of bacterial extracts. Anti-PhtD antibody was used to probe extracts from the PhtABDE⁻ quadruple mutant (A), the PhtE⁻ mutant (B), PhtD⁻ mutant (C), PhtB⁻ mutant (D), PhtA⁻ mutant (E), and the wild-type (F) strains. The position of the different Pht bands is indicated on the right, and a molecular mass mark is on the left side of the picture.

FIG. 6. Growth curves of 4/CDC wild-type strain and Pht-deficient mutants in MS medium (a). The growth curves of the wild-type, PhtD-deficient and Pht quadruple mutant were also determined in MS with or without $Zn^{2+}$ 200 µM (b), $Mn^{2+}$ 200 µM (c), or $Fe^{2+}$ 200 µM (d). Each figure depicts the results of one experiment representative of three.

Figure 7B:
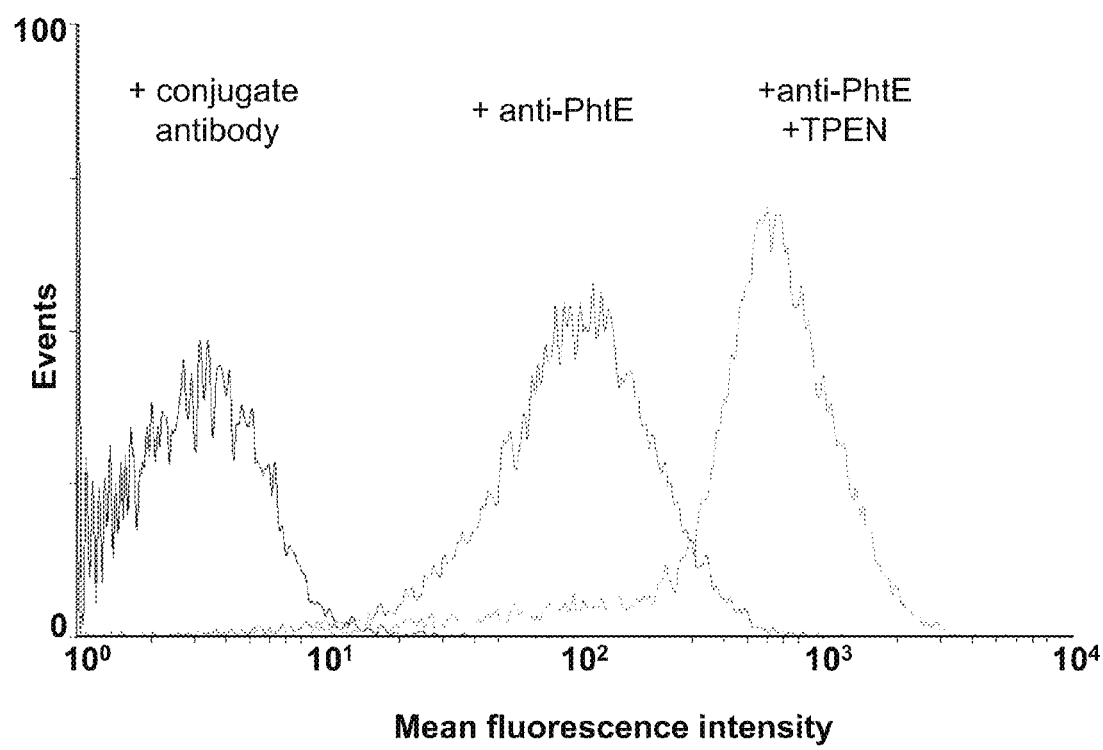
Figure 7C:
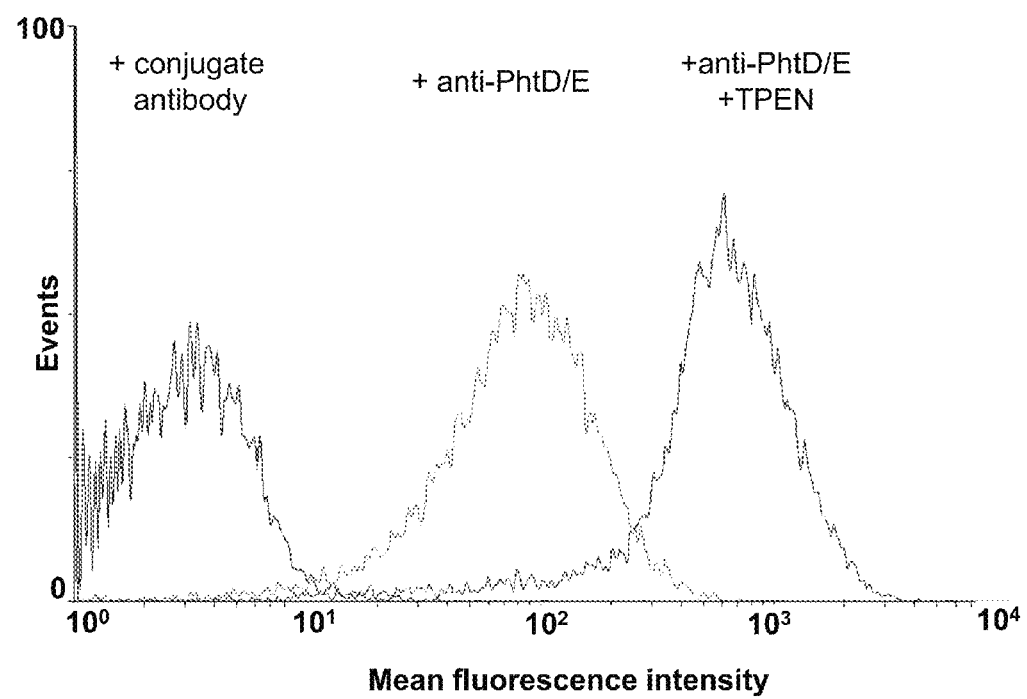

FIG. 7. WU2 bacterial cells were cultured with or without TPEN 30 µM, a zinc chelator. Next, cells were probed with anti-PhtB/D (a), anti-PhtE (b), anti-PhtD/E (c), or anti-type 3 polysaccharide (d) antibodies followed by AlexaFluor-conjugated goat anti-mouse secondary antibody before they were analyzed by flow cytometry. As controls, cells were incubated with the secondary conjugate antibody. Representative FACS plots of the different conditions are shown.

Figure 8:
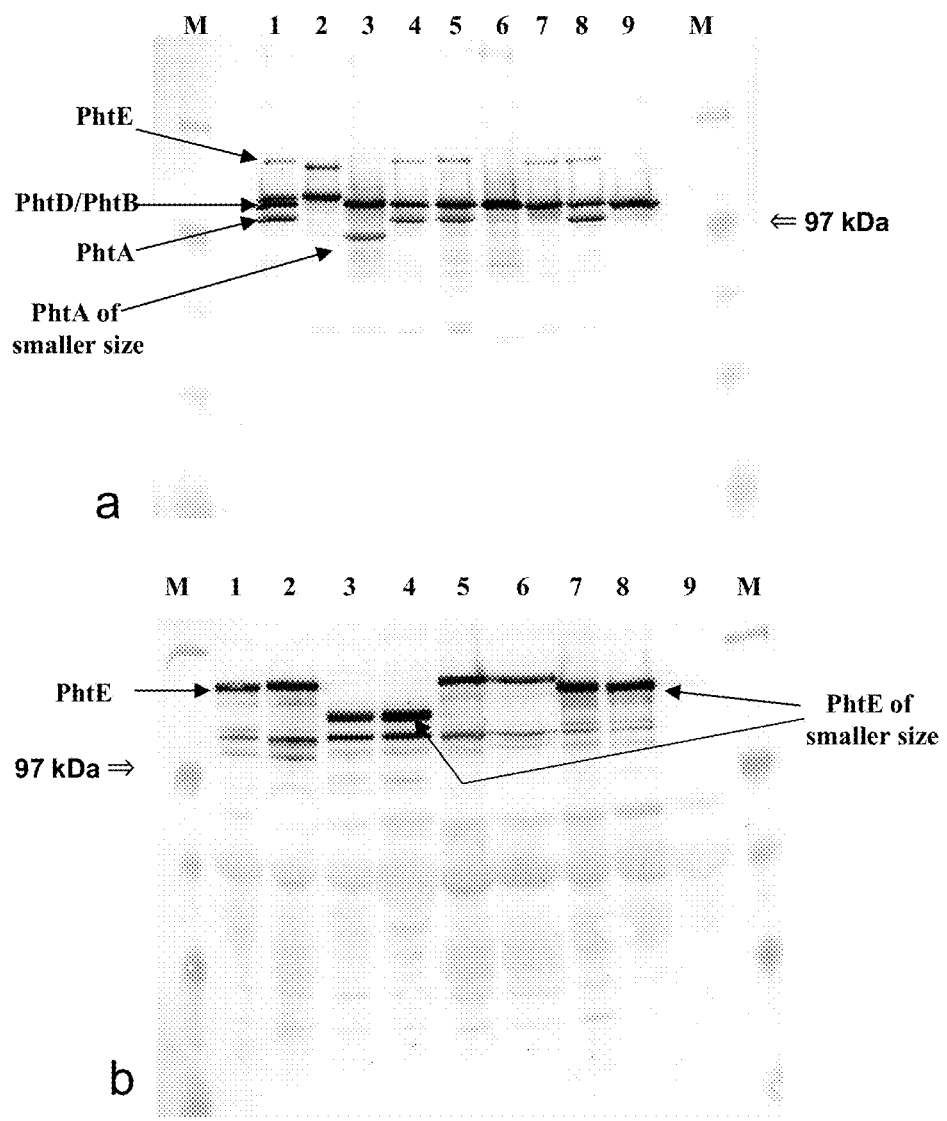

FIG. 8. Western blot analysis. Whole-cell extracts were submitted to SDS-PAGE followed by immunoblotting. Nine different strains were probed with a polyclonal anti-PhtD (a), and 8 with a polyclonal anti-PhtE (b). Molecular mass marker is shown.

FIG. 9. Signal sequences comparison of PhtX family members. The shaded areas identify amino acids which are conserved in at least ⅔ PhtX family members.

Figure 10:
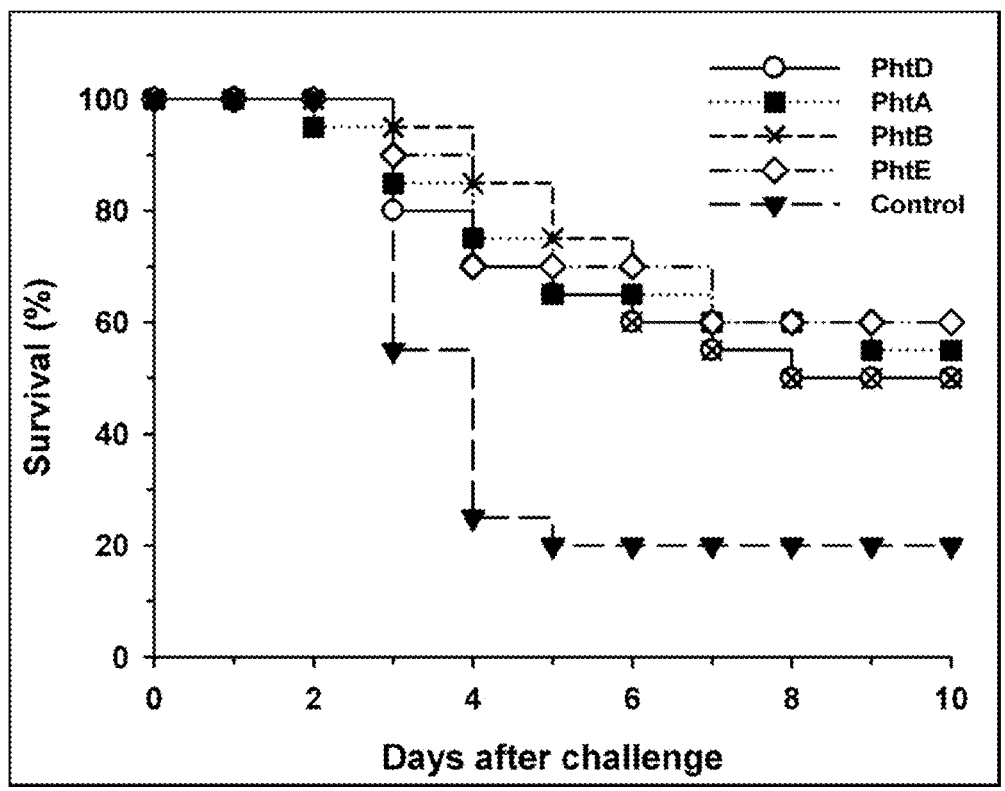

FIG. 10. Mice survival upon lethal *S. pneumoniae* intranasal challenge. Mice (n=20/group) were immunized with AS02-adjuvanted PhtD, PhtA, PhtB, PhtE or AS02 alone (control) before they were challenged with the type 3/43 pneumococcal strain. Statistical analyses were carried out with the logrank test, compared with control: PhtD, p=0.0126; PhtA, p=0.0103; PhtB, p=0.0038; PhtE, p=0.0033.

Figure 11:
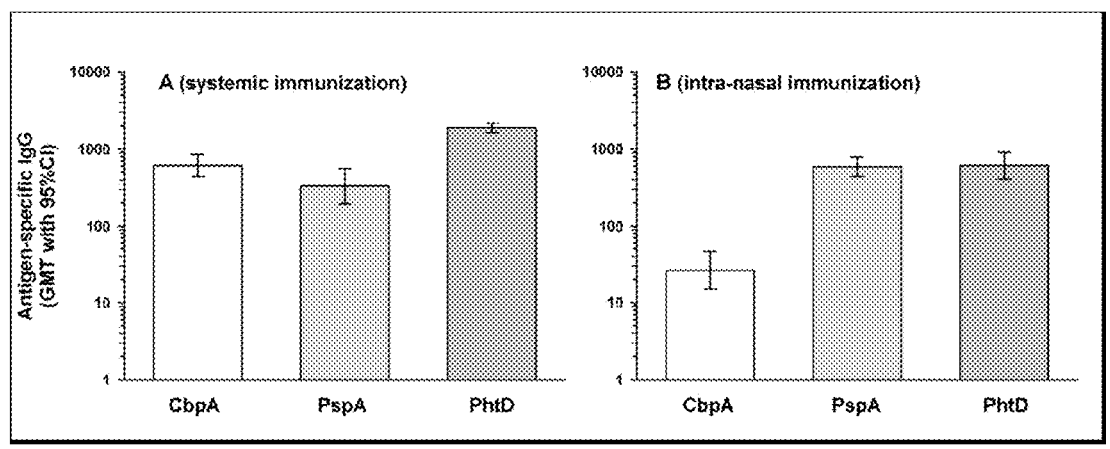

FIG. 11. Antibody levels after immunization. A.) Mice were immunized systemically with AS02-adjuvanted CbpA, PspA, or PhtD. B) Mice were immunized intra-nasally with LT-adjuvanted CbpA, PspA or PhtD. In both cases, blood was taken on day 42, and the levels of specific antibodies were measured by ELISA.

Figure 12:
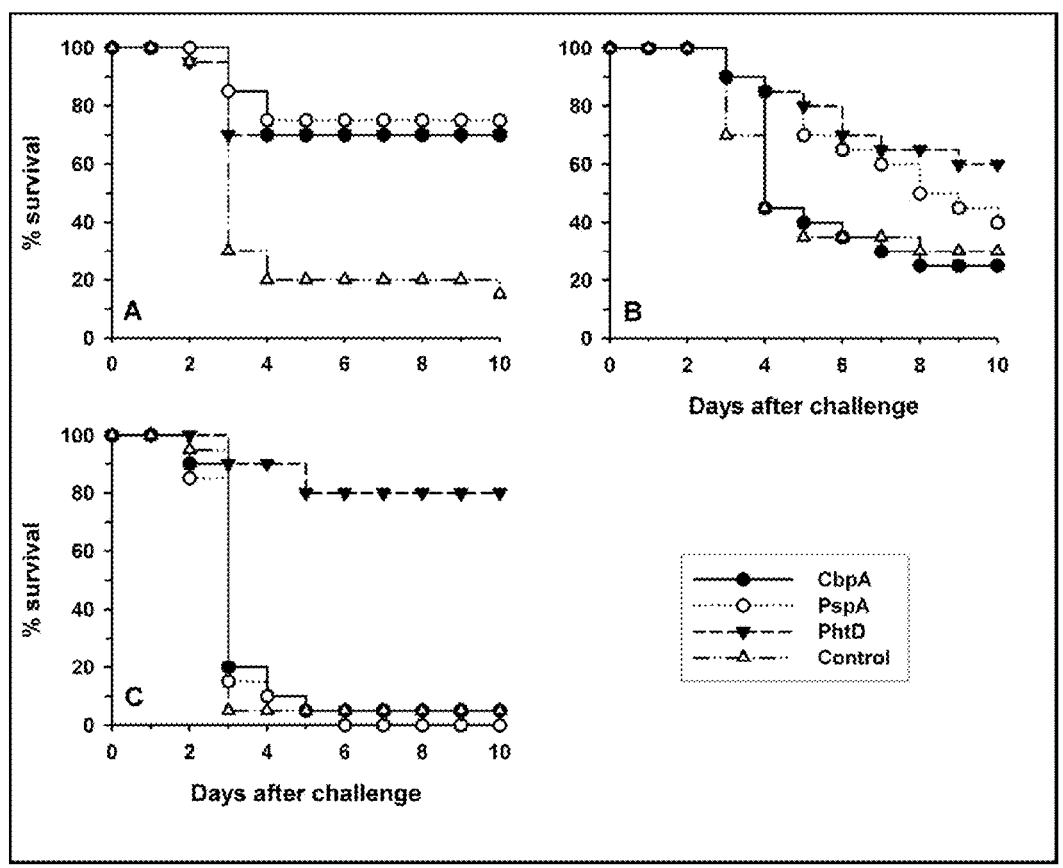

FIG. 12. Mice survival upon lethal *S. pneumoniae* intranasal challenge. Mice were immunized with AS02-adjuvanted CbpA, PspA, PhtD or AS02 alone (control) before they were challenged with the type 2/D39 (A), type 3/43 (B), or type 4/CDC (C) pneumococcal strains. Statistical analyses were carried out with the logrank test, compared with control: (A) CbpA, p=0.0002; PspA, p=0.0001; PhtD, p=0.0009. (B) CbpA, p=0.885; PspA, p=0.184; PhtD, p=0.027. (C) CbpA, p=0.825; PspA, p=0.538; PhtD, p<0.0001.

Figure 13:
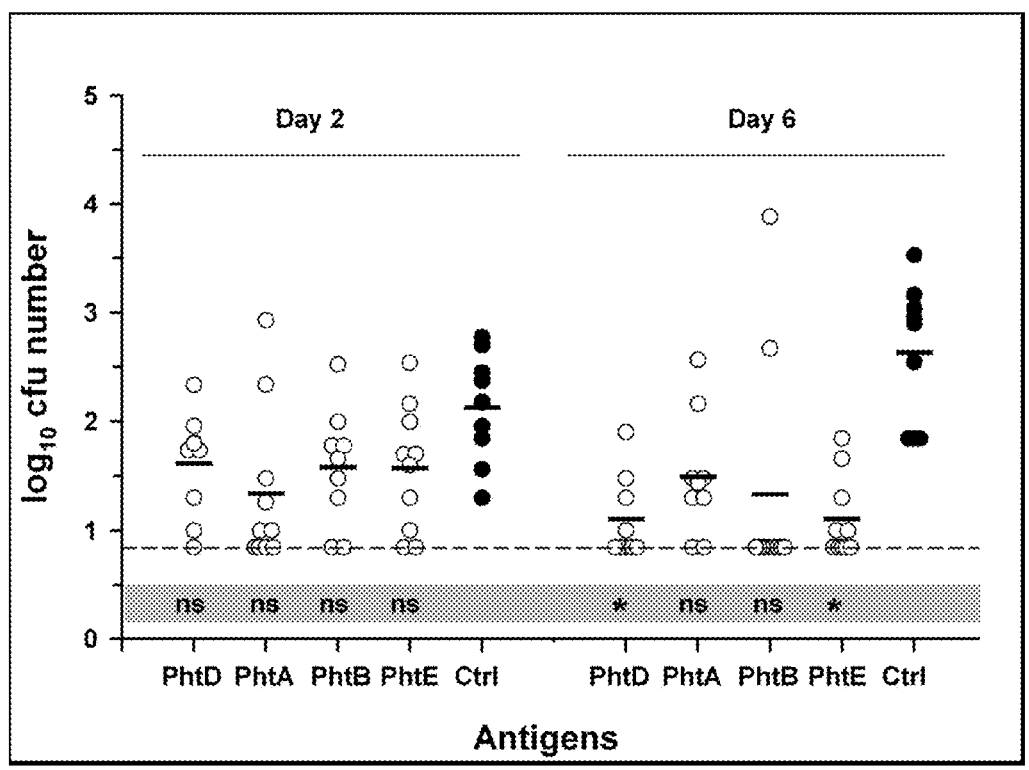

FIG. 13. Vaccine efficacy in a *S. pneumoniae* naso-pharyngeal colonization model. Balb/c mice were immunized with PhtD, PhtA, PhtB, PhtE, or LT alone (Ctrl), before they were intranasally challenged with the 2/D39 pneumococcal strain. Bacterial colonies were counted in nasal washings at day 2 and at day 6 post-challenge, and expressed as log 10 mean cfu. Each dot represents a mouse. Black horizontal bars are geometric means. Dashed line indicates limit of detection (at 0.84). Statistical analyses were carried out per day with ANOVA. All significant differences, compared with control, are shown. * p<0.05; ns: not significant.

Figure 14:
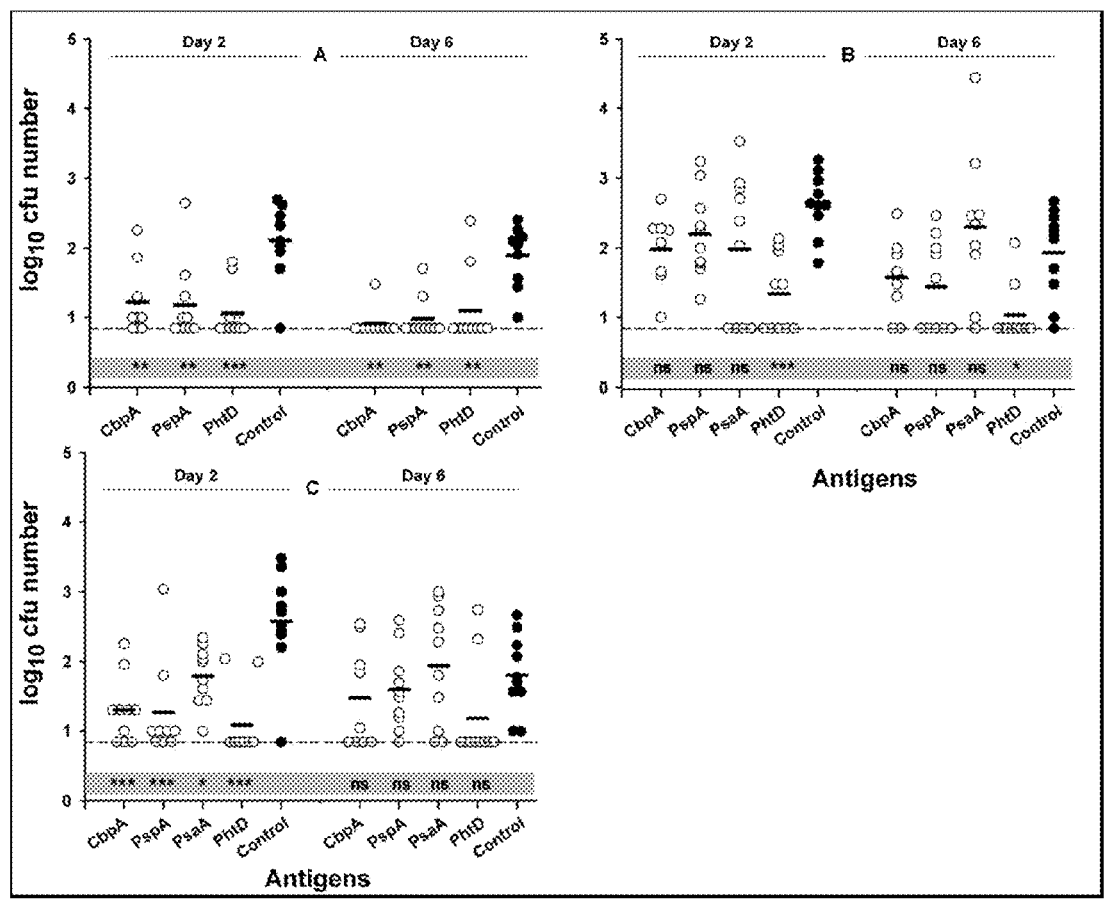

FIG. 14. Vaccine efficacy in a *S. pneumoniae* naso-pharyngeal colonization model. Balb/c mice were immunized with either CbpA, PspA, PhtD, PsaA, or LT alone (Control), before they were intranasally challenged with either the 2/D39 (A), the 4/CDC (B), or the 6B/CDC (C) pneumococcal strain. Bacterial colonies were counted in nasal washings at day 2 and at day 6 post-challenge, and expressed as log 10 mean cfu. Each dot represents a mouse. Dashed lines indicate limit of detection (at 0.84). Black horizontal bars are geometric means. Statistical analyses were carried out per day with ANOVA. All significant differences, compared with control, are shown. *p<0.05; p<0.01; *p<0.001, ns: not significant.

Figure 15:
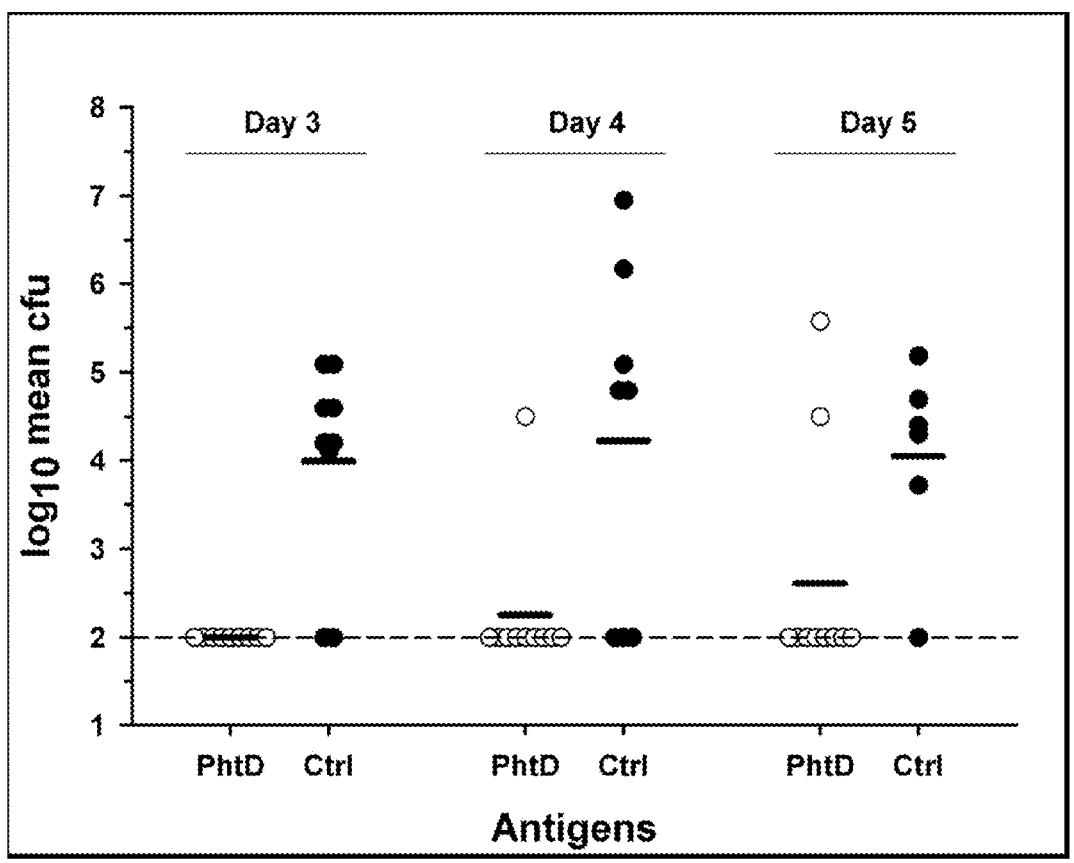

FIG. 15. Vaccine efficacy in a *S. pneumoniae* lung colonization model. CBA/J mice were immunized with AS02-adjuvanted PhtD or with AS02 only (Ctrl), before they were challenged with the moderately virulent 19F/2737 pneumococcal strain. Lungs were taken at day 3, 4 or 5 post-challenge, and bacterial load was evaluated by colony counting (cfu). Each dot represents a mouse. Dashed line indicates limit of detection (at 2). Black horizontal bars are geometric means. The groups were compared with ANOVA2 over the three days, followed by Tuckey-HSD: p<0.0001.

DETAILED DESCRIPTION

The invention provides a method of treating or preventing *Streptococcus pneumoniae* infection wherein the *Streptococcus pneumoniae* infection occurs in an environment where the concentration of $Zn^{2+}$ and/or $Mn^{2+}$ is sufficiently low to upregulate the expression of at least one PhtX protein in the

*Streptococcus pneumoniae*; comprising the step of administering a pharmaceutically effective amount of the PhtX protein to a human patient.

Zn2+ and Mn2+ are present in a human body in both free and bound forms. Bound Zn2+ or Mn2+ is bound to proteins such as albumin and makes up the majority of these ions. On the other hand, a small amount of free Zn2+ or Mn2+ is present in body fluids such as blood, lymph, interstitial fluid or cerebrospinal fluid. The term "bound" relates to ions which are tightly associated with proteins such as albumin. The term "free" relates to ions which are not tightly associated with proteins such as albumin. Such free ions are more available for uptake by *S. pneumoniae*. In an embodiment, the method of the invention provides a method of treating or preventing *Streptococcus pneumoniae* infection wherein the *Streptococcus pneumoniae* infection occurs in an environment where the free concentration of $Zn^{2+}$ and/or $Mn^{2+}$ is sufficiently low to upregulate the expression of at least one PhtX protein in the *Streptococcus pneumoniae*. In an embodiment, the method of the invention provides a method of treating or preventing *Streptococcus pneumoniae* infection wherein the *Streptococcus pneumoniae* infection occurs in an environment where the bound and/or free concentration of $Zn^{2+}$ and/or $Mn^{2+}$ is sufficiently low to upregulate the expression of at least one PhtX protein in the *Streptococcus pneumoniae*.

Bt the term "sufficiently low to upregulate the expression of at least one PhtX protein" for the purposes of the invention, it is meant that the level of Zn2+ and/or Mn2+(bound and/or free) is:
  a) lower than that usually found in the equivalent position of a human body, such that the level of expression of at least one PhtX protein in *S. pneumoniae* present in that body, is higher than the level of expression of PhtX in *S. pneumoniae* found in the equivalent compartment of the body under normal conditions (i.e. in an individual with average Zn2+ or Mn2+ levels); or
  b) lower than that found in regions of high Zn2+ availability of the body such that the level of expression of at least one PhtX protein in *S. pneumoniae* present in that location, is higher than the level of expression of PhtX in *S. pneumoniae* found in the region of high Zn2+ availability of the body in the same individual.

In an embodiment, the level of bound Zn2+ is reduced. In an embodiment, the level of free Zn2+ is reduced.

Situation a) may be achieved through a decrease in the overall levels of Zn2+ and/or Mn2+ whereas situation b) may be achieved by the *S. pneumoniae* infection occurring at a site which has comparatively low levels of Zn2+ and/or Mn2+.

A PhtX protein is a member of the histidine triad family of proteins. The PhtX protein is optionally the full length protein but may be a fragment of the protein or a fragment or fusion protein comprising at least one fragment or full length PhtX protein. The PhtX protein expressed in *S. pneumoniae* will be a full length protein, however the PhtX protein administered to a human patient is optionally a full length PhtX protein, a fragment of a PhtX protein or a fusion protein comprising at least one PhtX protein or fragment thereof.

In an embodiment, the PhtX protein is selected from the group consisting of PhtA, PhtB, PhtD and PhtE. In an embodiment, the PhtX protein is PhtD.

The present invention relates to members of the polyhistidine triad family (Pht) proteins, fragments or fusion proteins thereof. The PhtA, PhtB, PhtD or PhtE proteins may have an amino acid sequence sharing 80%, 85%, 90%, 95%, 98%, 99% or 100% identity with a sequence disclosed in WO 00/37105 or WO 00/39299 (e.g. with amino acid sequence 1-838 or 21-838 of SEQ ID NO: 4 of WO 00/37105 for PhtD).

The Pht (Poly Histidine Triad) family comprises proteins PhtA, PhtB, PhtD, and PhtE. The family is characterized by a lipidation sequence, two domains separated by a proline-rich region and several histidine triads, possibly involved in metal or nucleoside binding or enzymatic activity, (3-5) coiled-coil regions, a conserved N-terminus and a heterogeneous C terminus. It is present in all strains of pneumococci tested. Homologous proteins have also been found in other Streptococci and *Neisseria*. It is understood, however, that the terms Pht A, B, D, and E refer to proteins having sequences disclosed in the citations above or below as well as naturally-occurring (and man-made) variants thereof that have a sequence homology that is at least 90% identical to the referenced proteins. Optionally it is at least 95% identical or at least 97% identical.

With regards to the PhtX proteins, PhtA is disclosed in WO 98/18930, and is also referred to Sp36. As noted above, it is a protein from the polyhistidine triad family and has the type II signal motif of LXXC. PhtD is disclosed in WO 00/37105, and is also referred to Sp036D. As noted above, it also is a protein from the polyhistidine triad family and has the type II LXXC signal motif. PhtB is disclosed in WO 00/37105, and is also referred to Sp036B. Another member of the PhtB family is the C3-Degrading Polypeptide, as disclosed in WO 00/17370. This protein also is from the polyhistidine triad family and has the type II LXXC signal motif. For example, an immunologically functional equivalent is the protein Sp42 disclosed in WO 98/18930. A PhtB truncate (approximately 79 kD) is disclosed in WO99/15675 which is also considered a member of the PhtX family. PhtE is disclosed in WO00/30299 and is referred to as BVH-3. Where any Pht protein is referred to herein, it is meant that immunogenic fragments or fusions thereof of the Pht protein can be used. For example, a reference to PhtX includes immunogenic fragments or fusions thereof from any Pht protein. A reference to PhtD or PhtB is also a reference to PhtDE or PhtBE fusions as found, for example, in WO0198334.

The method of treatment or use of the invention may involve the administration of the full length PhtX protein, a fragment of the PhtX protein or a fusion protein containing at least 1 or 2 fragment(s) of PhtX proteins. Where fragments of Pht proteins are used (separately or as part of a fusion protein), each fragment optionally contains one or more histidine triad motif(s) and/or coiled coil regions of such polypeptides. A histidine triad motif is the portion of polypeptide that has the sequence HxxHxH where H is histidine and x is an amino acid other than histidine. A coiled coil region is a region predicted by "Coils" algorithm Lupus, A et al (1991) Science 252; 1162-1164. In an embodiment the or each fragment includes one or more histidine triad motif as well as at least one coiled coil region. In an embodiment, the or each fragment contains exactly or at least 2, 3, 4 or 5 histidine triad motifs (optionally, with native Pht sequence between the 2 or more triads, or intra-triad sequence that is more than 50, 60, 70, 80, 90 or 100% identical to a native pneumococcal intra-triad Pht sequence—e.g. the intra-triad sequence shown in SEQ ID NO: 4 of WO 00/37105 for PhtD). In an embodiment, the or each fragment contains exactly or at least 2, 3 or 4 coiled coil regions. In an embodiment a Pht protein disclosed herein includes the full length protein with the signal sequence attached, the mature full length protein with the signal peptide (for example 20 amino acids at N-terminus) removed, naturally occurring variants of Pht protein and immunogenic fragments of Pht protein (e.g. fragments as described above or polypeptides comprising at least 15, 20, 30, 40, 50, 125, 150, 175, 200, 250, 300, 350, 400, 450 or 500 contiguous amino acids from an amino acid sequence in WO00/37105 (SEQ ID NOs 4, 6, 8 or 10) or WO00/39299 (SEQ ID NOs 2, 4, 6, 8, 10 or 14) wherein said polypeptide is capable of eliciting an immune response specific for said amino acid sequence in WO00/37105 or WO00/39299. In an embodiment, the PhtX protein is a fragment described in WO 09/12588, for example those comprising or consisting of the sequences of SEQ ID NO: 2, 3 or 4.

In particular, the term "PhtD" as used herein includes the full length protein with the signal sequence attached, the mature full length protein with the signal peptide (for example 20 amino acids at N-terminus) removed, naturally occurring variants of PhtD and immunogenic fragments of PhtD (e.g. fragments as described above or polypeptides comprising at least 15 or 20 contiguous amino acids from a PhtD amino acid sequence in WO00/37105 or WO00/39299 wherein said polypeptide is capable of eliciting an immune response specific for said PhtD amino acid sequence in WO00/37105 or WO00/39299 (e.g. SEQ ID NO: 4 of WO 00/37105 or SEQ ID NO: 14 of WO 00/39299 for PhtD). All forms of PhtD mentioned above can be used in the present invention.

In an embodiment of the invention, the method of treatment or prevention is aimed at *S. pneumoniae* growing in the blood of the patient, for example for treatment or prevention of septicemia or bacteraemia. In an embodiment, the level of the free concentration of $Zn^{2+}$ in the blood is less than 10 nM, 7 nM, 5 nM, 3 nM, 2 nM, 1 nM, 700 pM, 500 pM, 300 pM, 200 pM 100 pM, 70 pM, 50 pM, 30 pM, 20 pM or 10 pM as measured from blood serum. The level of $Zn^{2+}$ may be measured by preparing a serum sample from a blood sample using standard procedures and analysing the sample using graphite furnace absorbance spectrophotometer (GF-AAS) or by using atomic absorption spectroscopy for example by using a Vista AX-CCD simultaneous ICP-AES spectrometer.

In an embodiment of the invention, the bound and free concentration of $Zn^{2+}$ in the blood is less than 5, 3, 2, 1, 0.5, 0.3, 0.2 or 0.1 mg/l or less than 20, 18, 15, 12, 10, 8, 5, 3, 2, 1, 0.5 or 0.1 µM as measured from blood serum. The level of $Zn^{2+}$ may be measured by preparing a serum sample from a blood sample using standard procedures and analysing the sample using graphite furnace absorbance spectrophotometer (GF-AAS) or by using atomic absorption spectroscopy for example by using a Vista AX-CCD simultaneous ICP-AES spectrometer.

In an embodiment of the invention, the free concentration of $Mn^{2+}$ in the blood is less than 10 nM, 7 nM, 5 nM, 3 nM, 2 nM, 1 nM, 700 pM, 500 pM, 300 pM, 200 pM 100 pM, 70 pM, 50 pM, 30 pM, 20 pM or 10 pM as measured from blood serum. The level of $Mn^{2+}$ may be measured by preparing a serum sample from a blood sample using standard procedures and analysing the sample using atomic absorption spectroscopy for example by using a Vista AX-CCD simultaneous ICP-AES spectrometer.

In an embodiment of the invention, the bound and free concentration of $Mn^{2+}$ in the blood is less than 5, 3, 2, 1, 0.5, 0.3, 0.2 or 0.1 mg/l or less than 20, 18, 15, 12, 10, 8, 5, 3, 2, 1, 0.5, 0.2 or 0.1 µM as measured from blood serum. The level of $Mn^{2+}$ may be measured by preparing a serum sample from a blood sample using standard procedures and analysing the sample using atomic absorption spectroscopy for example by using a Vista AX-CCD simultaneous ICP-AES spectrometer.

In an embodiment of the invention, the method of treatment or prevention is aimed at *S. pneumoniae* growing in the lung of the patient, for example the treatment or prevention of pneumonia. In an embodiment, the free concentration of $Zn^{2+}$ in the lung is less than 300, 200, 100, 80, 50, 20, 10, 5, 3 or 1 µg/kg as measured from a bronchial lavage. In an embodiment, the free concentration of $Mn^{2+}$ in the lung is less than 300, 200, 100, 80, 50, 20, 10, 5, 3 or 1 µg/kg as measured from a bronchial lavage. Optionally, the level of $Zn^{2+}$ or $Mn^{2+}$ is measured from a tissue sample in which case the concentration of $Zn^{2+}$ (or $Mn^{2+}$) in the lung tissue is less than 20, 15, 10, 5, 2 or 1 µg/g or 300, 200, 150, 100, 50, 20, 10, 5, 2, 1, 0.5 or 0.1 µM as measured from lung tissue. Similarly, the level of ions in the tissue sample can be measured by atomic absorption spectroscopy for example by using a Vista AX-CCD simultaneous ICP-AES spectrometer.

In an embodiment, the *S. pneumoniae* infection occurs in the a compartment of the ear, for example the middle ear, for example as an otitis media infection. In an embodiment, the level of $Zn^{2+}$ and/or $Mn^{2+}$ in the middle ear is less than 300, 200, 150, 100, 50, 20, 10, 5, 2, 1, 0.5, 0.2 or 0.1 µM.

In an embodiment, the *Streptococcus pneumoniae* infection occurs in the meninges, for example as a meningitis infection. In an embodiment the concentration of $Zn^{2+}$ in the cerebrospinal fluid is less than 1.5, 1, 0.75, 0.5, 0.25 or 0.1 µM or less than 100, 75, 50, 40, 25, or 10 µg/L. In an embodiment, the concentration of $Mn^{2+}$ in the cerebrospinal fluid is less than 2.5, 2, 1.5, 1 or 0.5 µg/L or less than 50, 25, 10 or 5 nM.

In an embodiment of the invention, the human patient has decreased level(s) of $Zn^{2+}$ and/or $Mn^{2+}$ as measured by broncheal lavage and/or blood test.

By "decreased level(s)" it is meant that the level of $Zn^{2+}$ and/or $Mn^{2+}$ as measured by broncheal lavage or blood test is less than that of an average human.

In an embodiment of the invention, the human patient to be treated with PhtX is $Zn^{2+}$ and/or $Mn^{2+}$ deficient. That is, the level of $Zn^{2+}$ and/or $Mn^{2+}$ is less than 90, 80, 70, 60, 50, 40, 30, 20, 10, 5 or 1% of the usual level for that body fluid, for example, blood serum, cerebrospinal fluid, interstitial fluid, bronchial lavage.

In an embodiment, the human patient is stressed. The stressed patient has lower levels of $Zn^{2+}$ and/or $Mn^{2+}$ in the body, for example in the blood, interstitial fluid, cerebrospinal fluid and/or lymph.

In an embodiment, the human patient has lower $Zn^{2+}$ and/or $Mn^{2+}$ levels in the body due to previous infection with a bacterial strain, for example a *S. pneumoniae, N. meningitidis, H. influenzae, S. aureus, S. epidermidis, C. difficile*, Group A *streptococcus*, Group B *streptococcus* and/or *M. catarrhalis* strain. The previous infection is optionally a chronic bacterial infection.

In an embodiment, the administration of PhtX, for example PhtD, is for the treatment or prevention of *Streptococcus pneumoniae* infection in the form of scepticaemia, bacteraemia, meningitis, otitis media or pneumonia.

The PhtX protein may also be beneficially combined with further antigens in the method or use of the invention. By combined, it is meant that the immunogenic composition comprises all of the proteins from within the following combinations, either as carrier proteins or as free proteins or a mixture of the two. For example, in a combination of two proteins as set out hereinafter, both proteins may be used as carrier proteins, or both proteins may be present as free proteins, or both may be present as carrier and as free protein, or one may be present as a carrier protein and a free protein whilst the other is present only as a carrier protein or only as a free protein, or one may be present as a carrier protein and the other as a free protein. Where a combination of three proteins is given, similar possibilities exist. Combinations include, but are not limited to, PhtD+NR1×R2, PhtD+NR1×R2-Sp91Cterm chimeric or fusion proteins, PhtD+Ply, PhtD+Sp128, PhtD+PsaA, PhtD+PspA, PhtA+NR1×R2, PhtA+NR1×R2-Sp91Cterm chimeric or fusion proteins, PhtA+Ply, PhtA+Sp128, PhtA+PsaA, PhtA+PspA, R1×R2+PhtD, R1×R2+PhtA. Optionally, NR1×R2 (or R1×R2) is from CbpA or PspC. Optionally it is from CbpA. Other combinations include 3 protein combinations such as PhtD+NR1×R2+Ply, and PhtA+NR1×R2+PhtD. In one embodiment, the vaccine composition comprises detoxified pneumolysin and PhtD or PhtDE as carrier proteins. In a further embodiment, the vaccine composition comprises detoxified pneumolysin and PhtD or PhtDE as free proteins. In an embodiment, the combination of proteins comprises PhtD and pneumolysin or PhtD and detoxified pneumolysin. In an embodiment, the method or use of the invention uses a combination of PhtD, detoxified pneumolysin and at least one *S. pneumoniae* capsulat saccharide, preferably conjugated to a carrier protein.

An aspect, the present invention provides an immunogenic composition comprising a PhtX protein and at least 4, 5, 6, 7, 8, 9, 10, 12, 14 1, 5, 16, 17, 18 or 20 *S. pneumoniae* capsular saccharide conjugates containing saccharides from different *S. pneumoniae* serotypes. In such an embodiment, at least one saccharide is conjugated to a PhtX protein such as PhtD or fusion protein thereof and the immunogenic composition is capable of eliciting an effective immune response against PhtX, for example PhtD. In a further aspect of the invention, the immunogenic composition comprises at least 4, 5, 6, 7, 8, 9, 10, 12, 14, 15, 16, 17, 18 or 20 *S. pneumoniae* capsular saccharide conjugates containing saccharides from different *S. pneumoniae* serotypes and a PhtX protein, for example PhtD as a free or unconjugated protein.

In an embodiment, the immunogenic composition of the invention comprises pneumolysin. The pneumolysin is preferably detoxified, for example by chemical treatment or by mutation of at least one amino acid.

The present invention further provides an immunogenic composition containing a pharmaceutically acceptable excipient and/or an adjuvant.

The immunogenic compositions of the present invention may be adjuvanted, particularly when intended for use in an elderly population but also for use in infant populations. Suitable adjuvants include an aluminum salt such as aluminum hydroxide gel or aluminum phosphate or alum, but may also be other metal salts such as those of calcium, magnesium, iron or zinc.

The adjuvant is optionally selected to be a preferential inducer of a TH1 type of response. Such high levels of Th1-type cytokines tend to favour the induction of cell mediated immune responses to a given antigen, whilst high levels of Th2-type cytokines tend to favour the induction of humoral immune responses to the antigen.

The distinction of Th1 and Th2-type immune response is not absolute. In reality an individual will support an immune response which is described as being predominantly Th1 or predominantly Th2. However, it is often convenient to consider the families of cytokines in terms of that described in murine CD4+ve T cell clones by Mosmann and Coffman (Mosmann, T. R. and Coffman, R. L. (1989) TH1 and TH2 cells: different patterns of lymphokine secretion lead to different functional properties. (Annual Review of Immunology, 7, p 145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of 11-4, IL-5, IL-6, IL-10. Suitable adjuvant systems which promote a predominantly Th1 response include: Monophosphoryl lipid A or a derivative thereof (or detoxified lipid A in general—see for instance WO2005107798), particularly 3-de-O-acylated monophosphoryl lipid A (3D-MPL) (for its preparation see GB 2220211 A); and a combination of monophosphoryl lipid A, optionally 3-de-O-acylated monophosphoryl lipid A, together with either an aluminum salt (for instance aluminum phosphate or aluminum hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-B1].

An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21, 3D-MPL and tocopherol in an oil in water emulsion is described in WO 95/17210. In one embodiment the immunogenic composition additionally comprises a saponin, which may be QS21. The formulation may also comprise an oil in water emulsion and tocopherol (WO 95/17210). Unmethylated CpG containing oligonucleotides (WO 96/02555) and other immunomodulatory oligonucleotides (WO0226757 and WO03507822) are also preferential inducers of a TH1 response and are suitable for use in the present invention.

Oil in water emulsion adjuvants per se have been suggested to be useful as adjuvant compositions (EP 0 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424, 067; EP 0 480 981 B). All of which form oil emulsion systems (in particular when incorporating tocols) to form adjuvants and compositions of the present invention.

In an embodiment, the oil emulsion (for instance oil in water emulsions) further comprises an emulsifier such as TWEEN 80 and/or a sterol such as cholesterol.

In an embodiment, the oil emulsion (optionally oil-in-water emulsion) comprises a metabolisible, non-toxic oil, such as squalane, squalene or a tocopherol such as alpha tocopherol (and optionally both squalene and alpha tocopherol) and optionally an emulsifier (or surfactant) such as Tween 80. A sterol (e.g. cholesterol) may also be included.

The method of producing oil in water emulsions is well known to the man skilled in the art. Commonly, the method comprises mixing the tocol-containing oil phase with a surfactant such as a PBS/TWEEN80™ solution, followed by homogenisation using a homogenizer, it would be clear to a man skilled in the art that a method comprising passing the mixture twice through a syringe needle would be suitable for homogenising small volumes of liquid. Equally, the emulsification process in microfluidiser (M110S Microfluidics machine, maximum of 50 passes, for a period of 2 minutes at maximum pressure input of 6 bar (output pressure of about 850 bar)) could be adapted by the man skilled in the art to produce smaller or larger volumes of emulsion. The adaptation could be achieved by routine experimentation comprising the measurement of the resultant emulsion until a preparation was achieved with oil droplets of the required diameter.

In an oil in water emulsion, the oil and emulsifier should be in an aqueous carrier. The aqueous carrier may be, for example, phosphate buffered saline.

The size of the oil droplets found within the stable oil in water emulsion are optionally less than 1 micron, may be in the range of substantially 30-600 nm, optionally substantially around 30-500 nm in diameter, and optionally substantially 150-500 nm in diameter, and in particular about 150 nm in diameter as measured by photon correlation spectroscopy. In this regard, 80% of the oil droplets by number should be within the ranges, optionally more than 90% and optionally more than 95% of the oil droplets by number are within the defined size ranges. The amounts of the components present in the oil emulsions of the present invention are conventionally in the range of from 0.5-20% or 2 to 10% oil (of the total dose volume), such as squalene; and when present, from 2 to 10% alpha tocopherol; and from 0.3 to 3% surfactant, such as polyoxyethylene sorbitan monooleate. Optionally the ratio of oil (e.g. squalene):tocol (e.g. α-tocopherol) is equal or less than 1 as this provides a more stable emulsion. An emulsifier, such as Tween80 or Span 85 may also be present at a level of about 1%. In some cases it may be advantageous that the vaccines of the present invention will further contain a stabiliser.

Examples of emulsion systems are described in WO 95/17210, WO 99/11241 and WO 99/12565 which disclose emulsion adjuvants based on squalene, α-tocopherol, and TWEEN 80, optionally formulated with the immunostimulants QS21 and/or 3D-MPL.

Thus in an embodiment of the present invention, the adjuvant of the invention may additionally comprise further immunostimulants, such as LPS or derivatives thereof, and/or saponins. Examples of further immunostimulants are described herein and in "Vaccine Design—The Subunit and Adjuvant Approach" 1995, Pharmaceutical Biotechnology, Volume 6, Eds. Powell, M. F., and Newman, M. J., Plenum Press, New York and London, ISBN 0-306-44867-X.

The vaccine preparations containing immunogenic compositions of the present invention may be used to protect or treat a mammal susceptible to infection, by means of administering said vaccine via systemic or mucosal route. These administrations may include injection via the intramuscular (IM), intraperitoneal (IP), intradermal (ID) or subcutaneous (SC) routes; or via mucosal administration to the oral/alimentary, respiratory, genitourinary tracts. Intranasal (IN) administration of vaccines for the treatment of pneumonia or otitis media is possible (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance pneumococcal saccharide conjugates could be administered separately, at the same time or 1-2 weeks after the administration of the any bacterial protein component of the vaccine for optimal coordination of the immune responses with respect to each other). For co-administration, the optional Th1 adjuvant may be present in any or all of the different administrations. In addition to a single route of administration, 2 different routes of administration may be used. For example, saccharides or saccharide conjugates may be administered IM (or ID) and bacterial proteins may be administered IN (or ID). In addition, the vaccines of the invention may be administered IM for priming doses and IN for booster doses.

The content of protein antigens in the vaccine will typically be in the range 1-100 µg, optionally 5-50 µg, e.g. in the range 5-25 µg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The vaccines or immunogenic compositions of the present invention may be stored in solution or lyophilized. In an embodiment, the solution is lyophilized in the presence of a sugar acting as an amorphous lyoprotectant, such as sucrose, trehalose, glucose, mannose, maltose or lactose. In an embodiment, the solution is lyophilized in the presence of a sugar acting as an amorphous lyoprotectant, and a bulking agent providing improved cake structure such as glycine or mannitol. The presence of a crystalline bulking agent allows for shortening freeze-drying cycles, in the presence of high salt concentration. Examples of such mixtures for use in lyophilisation of the immunogenic compositions or vaccines of the invention include sucrose/glycine, trehalose/glycine, glucose/glycine, mannose/glycine, maltose/glycine, sucrose/mannitol/trehalose/mannitol, glucose/mannitol, mannose/mannitol and maltose/mannitol. Typically The molar ratio of the two constituents is optionally 1:1, 1:2, 1:3, 1:4, 1:5 or 1:6. Immunogenic compositions of the invention optionally comprise the lyophilisation reagents described above.

The above stabilising agents and mixtures of stabilising agents can further include a polymer capable of increasing the glass transition temperature (Tg') of the formulation, such as poly(vinyl-pyrrolidone) (PVP), hydroxyethyl starch or dextran, or a polymer acting as a crystalline bulking agent such as polyethylene glycol (PEG) for example having a molecular weight between 1500 and 6000 and dextran.

Although the immunogenic compositions of the present invention may be administered by any route, administration of the described vaccines into the skin (ID) forms one embodiment of the present invention. Human skin comprises an outer "horny" cuticle, called the stratum corneum, which overlays the epidermis. Underneath this epidermis is a layer called the dermis, which in turn overlays the subcutaneous tissue. Researchers have shown that injection of a vaccine into the skin, and in particular the dermis, stimulates an immune response, which may also be associated with a number of additional advantages. Intradermal vaccination with the vaccines described herein forms an optional feature of the present invention.

The conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. No. 5,480, 381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503, 627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

The terms "comprising", "comprise" and "comprises" herein are intended by the inventors to be optionally substitutable with the terms "consisting of", "consist of" and "consists of", respectively, in every instance.

Embodiments herein relating to "vaccine compositions" of the invention are also applicable to embodiments relating to "immunogenic compositions" of the invention, and vice versa.

All references or patent applications cited within this patent specification are incorporated by reference herein.

In order that this invention may be better understood, the following examples are set forth. These examples are for purposes of illustration only, and are not to be construed as limiting the scope of the invention in any manner.

EXAMPLES

Methods

Animals

OF1 and CBA/J female mice used in this study were purchased from Charles River laboratories (Lyon, France). Balb/c mice were from Harlan (Horst, The Netherlands). All experiments and assays were performed at GlaxoSmithKline Biologicals (GSK, Rixensart, Belgium) in accordance with the Belgian national guidelines for animal experimentation.
Bacterial Strains and Culture Conditions.

The strain 2/D39 was kindly provided by J C Paton (University of Adelaide, Australia). The strains 4/CDC and 6B/CDC were obtained from the Center for Disease Control and Prevention (CDC), and the 19F/2737 strain from the American type culture collection (ATCC). The strain 3/43 was provided by E Yourassowski (Brugmann Hospital, University of Brussel, Belgium).

S. pneumoniae strain TIGR4 {Tettelin 2001} was kindly provided by Andrew Camilli (Tufts University School of Medicine, Boston, Mass., USA). The WU2 strain was kindly provided by David E Briles (University of Alabama at Birmingham, Birmingham, Ala., USA). The type 4 strain was obtained from the CDC (Center for Disease Control & Prevention).

Pneumococci were routinely grown in Todd-Hewitt broth (THB, Difco) with 0.5% (w/v) yeast extract at 37° C./8% $CO_2$. When appropriate, erythromycin and/or spectinomycin (Sigma-Aldrich, Bornem, Belgium) was added at a concentration of 0.2 and 250 µg/ml; respectively.

Escherichia coli DH5α and JM109 strains (Gibco BRL, Life Technology) were grown in Luria-Bertani broth (LBT, Difco) with or without 1.5% (w/v) Bacto-agar (Difco) at 37° C. for 16 h. When appropriate, erythromycin or spectinomycin was added to the growth medium at a concentration of 100 µg/ml.

For the study on Pht occurrence, besides 23 in-house and pneumococcal molecular epidemiology network (PMEN) strains, 34 isolates were provided by TJ Mitchell (Scotland), 6 by RE Gertz (USA), 2 by AB Brueggemann (UK) and 9 were from the American Type Culture Collection (ATCC).
Antigens CbpA (or PspC) was a truncated recombinant protein, as described in Brookes-Walter et al J. Infect. Dis. 67; 6533-6542 (1999), kindly provided by JC Paton. The protein was constructed from the sequence of the D39 strain and belongs thus to Glade A. PspA (Glade 2) and PsaA are recombinant proteins originating from the 2/D39 strain Ogunniyi et al Infect. Immun. 68; 3028-3033 (2000), both provided by JC Paton.
DNA Treatment and Analysis.

Escherichia coli plasmid DNA was obtained using Plasmid Midi or Mini Purification Kit (Qiagen Benelux, Venlo, The Netherlands). PCR products were purified with the QIAquick PCR Purification Kit and DNA digests were purified on 1% (w/v) agarose gel using the QIAquick Gel Extraction Kit (Qiagen). Restriction and ligation enzymes were obtained from New England BioLabs (Westburg, Leusden, Belgium). The Expand High Fidelity System (Roche, Mannheim, Germany) was used for each PCR reaction of these studies. All commercial products were used under conditions recommended by the suppliers.

DNA sequencing was carried out with the Big Dye Terminator Sequencing Kit on an Applied Biosystems automated DNA sequencer (model 3100) (Applied Biosystems Inc, Forster City, Calif., USA). Sequence analyzes were performed with the MacVector V6.5 software (Oxford Molecular Ltd., Madison) or the Vector NTI 7.1 software (Informax), and sequences compared to the available S. pneumoniae TIGR4 genome sequence (www.tigr.org) {Peterson 2001}.
S. pneumoniae Genomic DNA Extraction.

Chromosomal DNA from each strain was obtained by harvesting confluent overnight growth from one or two heavily inoculated blood agar plates into 1 ml of TE (10 mM Tris-HCl; 5 mM EDTA; pH 7.8). The bacterial suspension was centrifuged for 5 minutes at maximal speed in a microcentrifuge and the pellet was resuspended in 75 µl of TE. Cell lysates were obtained by sequential addition of 20 µl of lysozyme (100 mg/ml) and 20 µl of proteinase K (20 mg/ml) and incubation at 37° C., 45 minutes. Then, 500 µl of lysis buffer (10 mM Tris-HCl, pH 8.0; 0.14 M NaCl; 0.1 M sodium citrate; 1 mM EDTA, pH 8.0; 0.1% (w/v) sodium deoxycholate) was added and incubated for 10 minutes at room temperature. At the end of this incubation period, 250 µl of ammonium acetate (7.5 mM, pH 7.7) was added to crude lysate and incubated 10 minutes on ice. The viscous DNA was extracted twice with phenol/chloroform/isoamyl (25:24:1) and precipitated in isopropyl alcohol. The resulting DNA was washed with 70% (v/v) ethanol and resuspended in 50 µl TE containing 0.6 µl RNaseA (10 mg/ml). DNA suspensions were stored at 4° C.
RNA Isolation.

Total RNA was isolated from pneumococci grown from an optical density at 600 nm ($OD_{600}$) of 0.01 in THY to different $OD_{600}$ to evaluate gene expression at different growth phases (early log, $OD_{600}$=0.3; late log, $OD_{600}$=0.9; stationary, $OD_{600}$=1.2). Cells were centrifuged and resuspended in RNase-free Tris-EDTA containing 6 mg lysozyme ml$^{-1}$ and 1 mg sodium deoxycholate ml$^{-1}$, and incubated at room temperature for 10 min. After incubation, RNA isolation was performed with the QIAGEN RNeasy Mini Kit following manufacturer's instructions. Contaminating genomic DNA was eliminated by incubating RNA samples with 1 unit of DNase I per µg of RNA for 1 h at 37° C., followed by DNase inactivation with 2.5 mM EDTA for 10 min at 65° C. Total RNA was quantified using the Ribogreen® RNA Quantification Kit (Molecular Probes) following manufacturer's instructions.
5'-Rapid Amplification of cDNA End (RACE).

The method used to identify transcription starts was adapted from Ranasinghe & Hobbs {Ranasinghe 1998}. Briefly, a primer specific for the 3' end of the phtE gene was used to synthesize the first-strand complementary DNA (cDNA) from total RNA with the Superscript II reverse transcriptase (Invitrogen), following manufacturer's instructions. RNase A was then added for 1 h at room temperature to generate blunt 3' ends on the cDNA-RNA hybrid. The hybrid was inserted into EcoRV-digested pKS plasmid (Stratagene) using T4 DNA ligase (incubation overnight, 16° C.). A PCR reaction was set up to amplify the 5' end using another reverse 3' end-specific phtE primer and pKS-specific T7 promoter primer. Sequencing of the pKS-cDNA junction was performed to identify the +1 base.

Transcriptional Terminator Identification.

Terminator identification was performed using the Wisconsin Sequence Analysis Package version 10.1 (Genetics Computer Group) based on the method of Brendel & Trifonov {Brendel 1984}.

RT-PCR.

RT-PCR studies were performed as follows. RNA (2 µg) was first denatured for 5 min at 65° C. in a mixture containing 10 µM of 3'-end gene-specific reverse primer and 20 units of RNaseOut in a total volume of 10 µl. The reverse transcription reaction was then carried out by adding 5 mM dithiothreitol, 1 mM dNTP, 15 units of Thermoscript reverse transcriptase (Invitrogen), 1×cDNA synthesis buffer and RNase-free sterile water to a volume of 20 µl. The reverse transcription mixture was incubated at 56-58° C. for 1 hour, followed by reverse transcriptase denaturation for 5 min at 85° C. The RNA strand on the RNA-cDNA hybrids was degraded by incubating the reverse transcription solution at 37° C. for 20 min with 1 unit of RNase H. The PCR reaction was carried with 2 µl cDNA using different 5' gene-specific forward primers and the 3' gene-specific reverse primers used for the reverse transcription reaction (0.5 µM final concentrations), 0.2 mM dNTP, Taq DNA polymerase reaction buffer, 2.5 units of Taq DNA polymerase (Amersham Biosciences) and sterile water to a volume of 50 µl. The PCR cycle consisted of initial denaturation at 94° C. for 5 min, followed by 25-30 cycles of denaturation at 94° C. for 15-30 sec, annealing at 55° C. (phtE, phtD) or 63° C. (phtB, D, A) for 15-30 sec and extension at 72° C. for 1 min, and completed by a final extension step at 72° C. for 5-7 min. A negative control composed of RNA without reverse transcription reaction was also conducted to exclude DNA contamination in the RNA preparation. PCR products were separated by 1% (w/v) agarose gel electrophoresis and visualized by ethidium bromide staining.

Preparation of Pht Mutants.

Mutator vectors were constructed from the pGEM-T vector (Promega Benelux, Leiden, the Netherlands) that replicates in *E. coli* but not in *S. pneumoniae*. They contain recombinant zones that correspond to the upstream and downstream regions of the pht genes to be deleted, amplified by PCR, surrounding an antibiotic-resistance gene (primers and restriction sites used to construct the mutator vectors can be given on request). To prepare the quadruple Pht-deficient mutant, two different antibiotic resistance genes had to be used in order to combine deletion in the two different loci (locus phtD/phtE, and locus phtA/phtB). An erythromycin resistance gene (ermB), amplified from a derivative of the pJDC9 vector, was selected for the phtD/phtE locus. For the phtA/phtB locus, a spectinomycin resistance gene (aad(9) gene), purified from the pR350 plasmid (kindly provided by J Paton) was used.

Cloning was performed in DH5α or JM109 *E. coli* strains, with the different constructed plasmids and plated on LB agar with the respective antibiotics. Transformation of *E. coli* with plasmid DNA was carried out by standard methods with $CaCl_2$-treated cells {Hanahan 1985}.

The 4/CDC *S. pneumoniae* strain was prepared for transformation by two successive growing steps, before resuspension in CTM medium (10 g/l Casamino acids; 5 g/l tryptone; 5 g/l NaCL; 10 g/l yeast extract; 0.4 M $K_2HPO_4$; 20% glucose; 30 mg/ml glutamine; 1% BSA, 0.1 M $CaCL_2$; pH 7.8) aliquoting, and freezing in 15% glycerol. Those aliquots were used for transformation. After thawing, CSP-1 or CSP-2 (100 ng/ml in CTM medium) was added to induce competence, and the bacteria were incubated at 37° C. Different time points were taken (5, 10, 15, and 20 min) to optimise competence. After addition of 1 µg of mutator vector, cells were incubated at 32° C. for 30 min, with shaking, followed by 2-4 h at 37° C., under 5% $CO_2$. At last, bacteria were plated on blood agar with the appropriate antibiotics. For the quadruple mutant, the PhtD,E-KO strain was transformed with the plasmid that brings PhtA,B deficiency by using the same protocol as described above.

SDS-PAGE and Western Blot Analysis.

Heat-killed bacterial suspensions were obtained by harvesting the confluent overnight growth from 5 heavily inoculated blood agar plates into 1 ml of sterile PBS (0.14 M NaCl, 2.7 mM KCl, 10 mM $Na_2HPO_4$, 1.8 mM $KH_2PO_4$, pH 7.2), and an incubation step at 56° C. for 45 minutes. Then, sample buffer (60 mM Trizma base, 1% (w/v) SDS, 10% (v/v) glycerol, 0.01% (w/v) bromophenol blue, 2% (v/v) β-mercaptoethanol) was added to the heat-killed suspensions. Preparations were boiled for 5 minutes, centrifuged at maximum speed in a microcentrifuge for 2 minutes and separated by SDS-polyacrylamide gel electrophoresis (SDS-PAGE) as described by Laemmli {Laemmli 1970}. Proteins were electrophoretically transferred from acrylamide gels onto nitrocellulose membranes (Bio-Rad, Richmond, Calif.), as described {Towbin 1979}. Membranes were probed with a mouse polyclonal antibody raised against PhtD, followed by goat anti-mouse IgG conjugated to alkaline phosphatase (Promega Benelux.). Enzyme-labelled bands were visualized with a NBT/BCIP substrate system.

Culture Growth in Ion-Deficient Medium.

Wild-type 4/CDC strain, and corresponding PhtD- and Pht quadruple-deficient mutants were cultured under different conditions of ion depletion or supplementation in a chemically defined synthetic medium (MS){SICARD 1964}. MS medium was supplemented by increasing concentrations of, alternatively, $Mn^{2+}$, $Fe^{2+}$, $Fe^{3+}$, $Cu^{2+}$, or $Zn^{2+}$. Optical density at 600 nm was monitored during log-phase and at stationary phase. Results were compared with those of wild-type.

Wild-type WU2 strain was cultured with or without the Zn-specific chelator N,N,N',N',-tetrakis(2-pyridylmethyl) ethylenediamine (TPEN) to observe the effect of zinc depletion on Pht expression at the RNA (by RT-PCR) and protein (by flow cytometry) levels.

Flow Cytometry

WU2 bacteria were grown in THB+0.5% yeast extract at 37° C., 8% $CO_2$, up to log-phase. Alternatively, TPEN 30 µM, a zinc chelator, was added to the medium. After centrifugation, bacterial pellets were resuspended in a solution containing anti-PhtE, anti-PhtB/D, anti PhtD/E or anti-type 3 polysaccharide monoclonal antibodies as control. After 2 h at 4° C.; the solutions were centrifuged, the bacterial pellets were washed in PBS-BSA 2% before they were incubated for 1 h at room temperature in AlexaFluor™ (Molecular Probes)-conjugated goat anti-mouse secondary antibody in PBS-BSA 2%. After washing, cells were fixed in PBS-formaldehyde 0.25% and FACS analysis was performed. The median of surface fluorescence was recorded.

Determination of Pht Occurrence

In order to select representative strains of *S. pneumoniae*, the population structure was analysed according to the strain genotype as determined by MLST (Multi-Locus Sequence Type; www.mlst.net). Based on MLST isolate Sequence Type (ST), major clonal lineages were determined. For each group, a representative strain was selected for occurrence analysis, which was carried out by Western blotting on whole bacterial extracts with anti-PhtD polyclonal antibodies (cross-reactive with A, B and D) or anti-PhtE, and by PCR on pneumococcal genomic DNA using primers specific for PhtA, B, D or E.

DNA Sequencing for PhtD Conservation Analysis

DNA of 107 MLST-selected strains was PCR-amplified using PhtD-specific oligonucleotide primers. The 107 sequences were aligned by ClustalX program and the identity was calculated by the Superneedle program (percentage of identity is 100×(number of identities/length of shortest sequence).

Example 1

Characterization of the Pht Genes

Genomic Organization of the Pht Genes.

In a previous work, DNA sequencing of overlapping clones from a *S. pneumoniae* strain SP64 genomic library {Hamel 2004} and PCR analyses allowed deduction of the genomic organization of the pht genes and their neighbouring genes in this type 6B strain. The phtA and phtB genes, as well as the PhtD and the PhtE genes, were organized as a pair. BLAST analyses on the TIGR web site (www.tigr.org) {Peterson 2001} indicated that the two gene tandems were located about 161 kbp apart in the *S. pneumoniae* TIGR4 genome and that the genomic organization was identical to the one observed in the SP64 strain (FIG. 1). The same pht gene organization was also found in the 4/CDC strain and in the WU2 strain, with the exception that phtA is missing in the latter (data not shown). Sequencing of the pht genes surroundings on the TIGR4 strain DNA confirmed the latter observation (data not shown). Additional analysis demonstrated that phtA and phtB were separated by 157 bp, whereas phtD and phtE were separated by 209 bp in the TIGR4 strain, which was chosen for further work.

On the phtD-phtE tandem side, a gene presenting 72% sequence similarity to the group A and B streptococci lmb genes, coding for laminin-binding proteins (accession # AAK34689 {Ferretti 2001} and AAD13796 {Spellerberg 1999} respectively), was located 7 bp upstream of the phtD gene (FIG. 1). This gene product was also recently denominated as AdcAII, and described as an ABC transporter-like zinc-binding protein {Loisel 2008}. A 1392-bp ORF, located 142 bp upstream of the lmb gene homolog, codes for a protein presenting 64% sequence similarity with the *Bacillus subtilis* metabolite transporter YfnA protein (accession # D69814) and 81% similarity with a putative amino acid permease of *S. pyogenes* (accession # AAK33157) {Ferretti 2001, Kunst 1997}. A sequence presenting 79% identity with the first 481 bp of phtE (proposed phtF) was found 226 bp after the phtE stop codon (FIG. 1). This sequence also shows 72% identity with the phtA, B and D genes.

On the phtA-phtB tandem side, a 1332-bp ORF, presenting 73% sequence similarity with the *Streptococcus salivarius* ptsI gene (accession number P30299) {Gagnon 1992}, was located 253 bp upstream of the phtA gene (FIG. 1). This gene presented a frameshift in the TIGR4 strain that we sequenced compared to the ptsI gene found in the whole genome sequence (accession # AAK75285). No functional ORF was located immediately downstream of both gene pairs.

Example 2

Transcriptional Organization of pht Genes

The genomic organization of pht genes suggested that the tandem genes might be coordinately transcribed. Further studies were thus performed to examine this hypothesis. First, putative promoters and ribosome binding sites of pht genes were identified. The 5'-RACE on the phtE gene allowed the identification of its transcription start, from which the promoter region was deduced. The transcription start site (+1) was found to be located 96 bases upstream of the PhtE translation start site, downstream of typical *S. pneumoniae* −10 and −35 RNA polymerase binding sites {Morrison 1990} and upstream of a ribosome binding site (FIG. 2a). Similar sequence organization was found upstream of the phtA, phtB and yfnA genes, indicating the presence of putative promoters (FIGS. 2b, c and e). However, due to the close proximity of the lmb gene (7 bp), no promoter sequence was identified for the phtD gene. On the other hand, a sequence identical to the −35 sequences of the other pht genes was located upstream of the lmb gene (FIG. 2d). Ribosome binding sites were observed 5 to 7 bp upstream of all start codons.

Transcription termination sites of pht and adjacent genes were also identified. Computer analysis of predicted mRNA secondary structures suggested the presence of stem-loop terminator-like structures at the 3' ends of genes. Hairpin structures could form with calculated free energies of dissociation ($\Delta G$) of −9.4, −27.0, −16.8, and −21.6 kcal mol$^{-1}$ for phtB, phtD, phtA, and ptsI respectively, as determined by the method of Turner et al. (1988) {Turner 1988}(FIG. 3). In fact, the terminator identified for the phtD gene was identical to the one reported by the TIGR web site for ORF SP1003, which corresponds to the phtD gene homolog (www.tigr.org). No transcription terminators were identified by the TIGR group for the other pht or surrounding genes, probably reflecting differences in algorithms used by both studies. Most hairpins ended with a stretch of T residues as typically found in prokaryotic transcription terminators {Rosenberg 1979} and were located within 70 bp downstream of stop codons (FIG. 3). Interestingly, the phtE terminator sequence ($\Delta G$ of −4.7 kcal mol$^{-1}$) was located 1867 bp downstream of its stop codon and of the phtF gene, the latter ORF containing in-frame stop codons preventing its translation (FIG. 3a). No terminator sequences were identified downstream of yfnA and lmb genes.

The genomic organization suggested that phtE could be part of an operon composed of the yfnA, lmb, phtD, phtE and phtF genes. Nevertheless, the 5'-RACE (FIG. 2a) and terminator identification (FIG. 3a) indicated that phtE was the first gene transcribed on a bicistronic message, composed of phtE and phtF genes, which was confirmed by RT-PCR. The regions phtE to phtF were amplified by RT-PCR (FIG. 4a, lanes 4 and 6), whereas no amplification product was obtained with primer pair specific to the region between genes phtD and phtE (FIG. 4a, lane 5), indicating transcriptional termination downstream of phtD (FIG. 3c).

As shown in FIG. 4a (lanes 1 to 3), RT-PCR amplified the regions yfnA to phtD. Moreover, Loisel et al. {Loisel 2008} have demonstrated that this phtD transcript also encodes, in addition to yfnA, lmb and phtD, the two genes upstream yfnA (ccdA that is involved in the biogenesis of cytochrome c and spr0904 that displays similarity with thioredoxine). Interestingly, the identification of a putative promoter upstream of the lmb gene (FIG. 2d) suggested transcriptional coupling of the phtD and lmb genes.

Results obtained for phtB and phtA genes showed that they were transcribed as monocistronic mRNAs, as was suggested by promoter (FIGS. 2b and c) and terminator sites identification (FIGS. 3b and d). Analysis of the transcriptional organization of phtA and phtB by RT-PCR revealed a phtB-specific amplicon with phtB-specific primers (FIG. 4a, lane 7). No amplification product was obtained by RT-PCR with primers amplifying the region between phtA and phtB (FIG. 4a, lane 8), indicating a monocistronic organization of the phtA and phtB genes. Terminator site identification (FIG. 3e) indicated that ptsI is transcribed as a monocistronic message, which also confirmed that phtA is not part of a polycistronic transcript.

Example 3

Construction and Use of Pht Mutants

Characterization of the Mutants.

The mutants PhtA⁻, PhtB⁻, PhtD⁻, PhtE⁻, and the quadruple mutant PhtABDE⁻ were constructed. To assess the accuracy of the recombination, the genomic DNA of the mutant strains was purified and the recombinant regions were sequenced (data not shown). Furthermore, the mutants were phenotypically characterized by immunoblotting, using a mouse polyclonal anti-PhtD antibody (FIG. 5). All four Pht isotypes were recognized by this antibody. However, PhtE bands were fainter, confirming the greatest divergence of this Pht from the three others.

The Influence of Various Ions on Bacterial Growth

The growth of the Pht quadruple mutant was dramatically decreased in MS medium, compared to that of the wild-type strain and of the different Pht single mutants (FIG. 6a). When the medium was supplemented with up to 200 µM of $Fe^{2+}$, $Zn^{2+}$, or $Mn^{2+}$, the growth of the wild-type and of the PhtD-deficient mutant was slightly ameliorated (growth rate vs MS alone: 96-130%). In contrast, the behavior of the quadruple mutant was striking. While the addition of 200 µM of $Fe^{2+}$ to MS only induced a 25.3% increase of growth (FIG. 6d), the same concentration of $Zn^{2+}$ or $Mn^{2+}$ restored the growth capacity of the quadruple mutant (FIG. 6b,c). This represents up to 92.3% increase in growth rate, compared to that obtained in MS alone. However, this recovery of growth rate was delayed, only visible after overnight incubation, as no improvement was visible within the first hours of culture. The addition of $Mg^{2+}$ did not restore growth completely at 200 µM, as did $Zn^{2+}$ or $Mn^{2+}$, but similar increase in growth rates were obtained when 1 mg/ml of $Mg^{2+}$ was added to MS (data not shown). The addition of high concentrations of $Cu^{2+}$ was toxic for wild-type and mutant strains (data not shown).

Example 4

The Effect of Zinc Depletion on Pht Expression

Figure 7D:
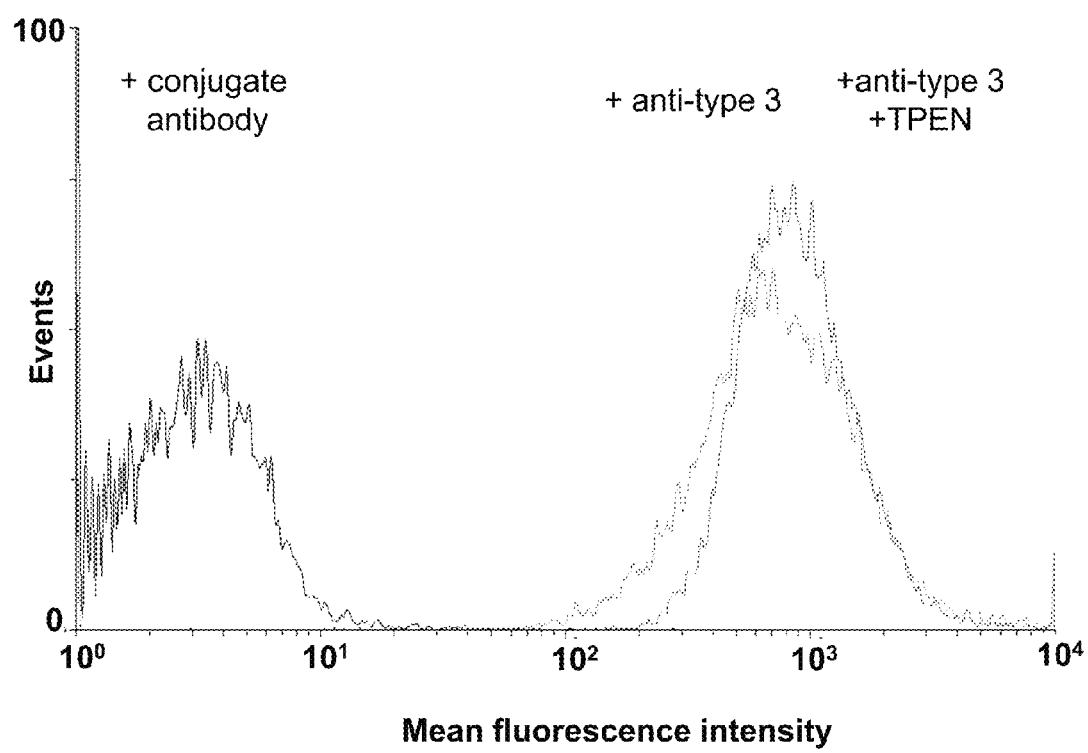

When the zinc chelator TPEN was added to the culture medium, the expression level of the Pht proteins was increased, as determined by flow cytometry experiments (FIG. 7a,b,c). As a control, no shift in mean fluorescence was observed with anti-type 3 polysaccharide antibody in the same conditions of zinc depletion (FIG. 7d). At the RNA level, we could measure, by RT-PCR, up to 25-fold increase in the phtE transcription level in the condition of zinc depletion (data not shown).

Example 5

Pht Occurrence in Pneumococcus

In total, 74 strains (including 23 PMEN and in-house strains) were investigated. In this set of representative strains, 18 clonal lineages were represented, 46 strains (61%) with 27 different ST belonged to the 3 major clonal groups (1, 11 and 23), 56 different ST were present, among which the more represented were 81, 90, 124, 156, 162 and 199 (22 strains), and 27 different serotypes were present among which the more represented were 19F, 6B, 3, and 23F (47% of all strains).

By PCR on genomic DNA, we found the genes for PhtD, PhtE, PhtB and PhtA in 100%, 97%, 81%, and 62% of the strains, respectively. Fifty-four percent of the strains were found to carry the four pht genes in their genome. On immunoblots with polyclonal antibodies raised against PhtD, we could detect PhtD in all strains. Likewise, the other Phts were found by immunoblotting in all strains that carry their respective genes. Notably, due to the highest genetic divergence, PhtE was better detected with a polyclonal antibody specifically raised against it (FIG. 8). Some peculiar Phts were found, such as a PhtE of a lower size (10-kDa smaller) in 6 isolates, and of an even smaller size (20-kDa less) in 8 strains. Likewise, 4 strains were found to produce a truncated PhtA (FIG. 8), which gene was not detected by PCR. Interestingly, these 4 strains also expressed the 20-kDa-truncated PhtE. At least, sequencing of the phtA/B locus of phtB negative strains has revealed that the only gene present in this locus was an hybrid between either phtA and phtB or phtA and phtD genes.

Interestingly, sequence analysis has demonstrated that the signal sequence encoded by pht genes was specific for each Pht family members. Indeed, the specific signal sequence of a Pht family member differ at least in one position to the signal sequence of another Pht family member (see table 1).

Next, it was attempted to determine whether links can be made between the Pht expression profile and the isolate genotype/serotype. In the strains analyzed, all serotype 2, 4, 14, 6B and 7F isolates possessed the 4 Phts, and all serotype 3, 9, 19F and 22F isolates lacked PhtA or carried a smaller PhtA.

About a potential link between MLST genotype and Pht expression profile, the following features could be determined: the 10-kDa-truncated PhtE was found mainly in the genotype ST 199 group. The serotypes of these strains are 19F, 19A, 15A, 1 and 6A. The 20-kDa-truncated PhtE was observed in 8 isolates that all belonged to the same clonal lineage (group 1), but carrying different serotypes (9, 19A, 19F, 14). At last, strains lacking PhtA were observed in different clonal lineages. Therefore, no major link between lack of PhtA and genotype was identified.

Example 6

PhtD Conservation

In the Pht occurrence study, PhtD was found to be present among all pneumococcal strains tested, which designates it as the best vaccine candidate among the Pht family. In this respect, it was found essential to determine the level of sequence conservation among pneumococcal strains. For that, DNA sequencing was carried out.

From the analysis of 107 strains (based on MLST classification), it was determined that the length of PhtD varies between 831 and 853 amino-acids with a molecular mass of around 100 kDa. PhtD was found to be highly conserved among the 107 strains tested and only 1 sequence displayed a stop for a truncated protein (strain 4/75). The proline-rich region contained 13-15 prolines for all strains (in 7 strains, only 11-13 prolines). Limited stretches of variability<4 amino acids were found in the sequence of PhtD.

Discussion

The Pht proteins are promising candidates to be incorporated in a vaccine against pneumococcal infectious diseases. In that respect, it appeared crucial to investigate how the expression of these proteins is regulated, in order to better define their role in pneumococcal pathogenesis.

Genome analysis showed that the four gene homologues are arranged in tandem. The presence of a fifth member, though truncated, of the pht gene family, downstream of the phtE gene was also evidenced, confirming the finding in a previous study {Adamou 2001}. It seems that this truncation is conserved since the same organization was found in the *S. pneumoniae* strain R6 genome (accession # AAK99714) {Hoskins 2001}.

Our study showed that the tandem organization of the pht genes does not correlate with a pht bicistronic transcription. None of these genes were co-transcribed with their related pht neighbor, under the conditions tested. Promoter and terminator analyses correlated well with traditional RT-PCR studies. We evidenced that the phtB, phtA and phtE genes all possess individual putative promoters and that mRNA transcription probably ends soon after the corresponding stop codons. On the other hand, a peculiarity of the phtD gene was observed. Indeed, no promoter was identified in-silico for phtD. Instead, promoters, but no transcription terminators, were identified for lmb and yfnA genes, two genes located upstream of phtD, which tended to indicate that those genes are organized in an operon system. This corroborates the recent finding that phtD may be expressed in a large operon system together with the 4 genes upstream {Loisel 2008}. Nevertheless, the fact that a promoter was identified for yfnA and for lmb indicates that transcription may start at these locations, which means that phtD-containing transcripts of different length may be produced. In addition, an adcR binding site was identified upstream of the lmb gene {Loisel 2008, Panina 2003}, which tend to say that a zinc-regulated bicistronic transcript with lmb and phtD may also exist, which has been suggested by other authors. Studies by Spellerberg et al. {Spellerberg 1999} showed that the group B streptococcal (GBS) lmb gene is co-transcribed with a gene whose product presents 67% sequence similarity with the first 225 (phtE) and first 228 (phtA, phtD and phtB) amino acids of pht gene products (accession # AF062533). A comparable genomic arrangement was also observed in the group A streptococcal (GAS) genome {Ferretti 2001}. Further, it was proposed that co-transcription of lmb and phtD might indicate a functional link, with the latter gene product being involved in pneumococcal adhesion and invasion {Panina 2003}.

It is interesting to note that the phtD gene can be transcribed as a polycistronic message with those two other genes, yfnA and lmb, that may be involved in transport and specific binding activities, respectively. Indeed, YfnA in *S pneumoniae* {Hoskins 2001}, and the homologous proteins in *B. subtilis* {Yamamoto 1997}, *S. pyogenes* {Ferretti 2001}, and *S. mutans* {Ajdic 2002} are thought to be amino-acid transporters, members of the superfamily of permeases. As to the Lmb protein, it has been described as an ABC transporter-like zinc-binding protein {Loisel 2008} and a putative laminin-binding protein {Spellerberg 1999}. Indeed, this protein demonstrates similarities with an adhesin family known as Lral, found initially in oral streptococci {Jenkinson 1994}, but since then discovered in other streptococci and genera {Cockayne 1998}. It was suggested that Lral-like proteins are involved in the colonization of human epithelium by streptococci and their subsequent invasion into the bloodstream {Elsner 2002}. It is not clear why yfnA, lmb, and phtD are associated in an operon system. One plausible hypothesis is that those three proteins are required at the same moment of the bacterial cyclus, for invasion or growth, for instance, without necessarily being associated in their functions. However, the determination of the role of the Pht proteins might give some clue for this genomic association. We can speculate that similarities between intra-species Pht proteins are indicative of interchangeable roles. It might also be that the proteins share similar functions through their homologous regions and, at the same time, exert distinct activities, even at different development phases of the bacterium. The results we have obtained in immunoblotting with protein extracts from the various Pht-deficient mutants that we have produced tend to show that there is no compensation for gene loss by increasing the level of expression of the remaining Pht gene products. This feature was also described recently at the RNA level, by using RT-PCR {Ogunniyi 2009}.

As already mentioned, all Pht proteins share histidine triad motifs {Adamou 2001, Hamel 2004, Zhang 2001}, thought to be involved in metal binding. Interestingly, it has been speculated that these motifs might be involved in zinc binding, especially to generate conformationally functional Pht proteins {Panina 2003}. The same authors also hypothesized that a zinc-restricted environment could induce the expression of the Pht proteins and favor *Streptococcus* colonization and invasion. In this context, we carried out experiments in which wild-type and Pht-deficient strains were cultured under different conditions of ion depletion and supplementation. In a minimal synthetic medium, wild-type and PhtD-deficient strains grew more slowly than in rich LB medium, but almost no growth of the quadruple Pht-deficient mutant was observed in the minimal medium. Strikingly, when $Zn^{2+}$ or $Mn^{2+}$ was added, and this was particularly visible at concentrations in the range of 20-200 µM, the growth of the quadruple mutant was restored up to that of the wild-type. However, our results show that the growth of the quadruple mutant was delayed, as compared with the wild-type.

These observations, besides confirming the requirement of $Zn^{2+}$ and $Mn^{2+}$ for bacterial growth, argue for a critical role of the Pht family in $Zn^{2+}$ and $Mn^{2+}$ uptake. The fact, as we have observed, that $Zn^{2+}$ deprivation induces de novo synthesis of proteins of the Pht family is a further argument to support a tight relation between Pht and $Zn^{2+}$. This regulation is likely to occur through AdcR protein that regulates zinc uptake in *S. pneumoniae*. Indeed, putative binding sites for AdcR protein have been found upstream of the phtA, phtB, and phtE genes, and of the lmb-phtD operon {Panina 2003}. Binding of AdcR, induced in conditions of high $Zn^{2+}$ concentrations, inhibits the transcription of the genes under its dependence. Upon direct or indirect zinc starvation conditions, hence reduction in intracellular concentration of this metal, repression by AdcR is relieved {Brenot 2007, Claverys 2001}. Conversely to that and to what we have observed in the present study, it was recently published that the addition of zinc in culture medium elicits Pht production {Ogunniyi 2009}. However, the two methods used were distinct in the sense that, in the present work, zinc was removed from a zinc-rich medium while Ogunniyi et al. added zinc to a zinc-poor medium. It is reasonable to estimate that Pht production is regulated in a bell-shaped way within a given range of zinc concentration. Also, the high zinc concentration effects observed by Ogunniyi et al {Ogunniyi 2009}, leading to increased Pht expression, may have little in vivo relevance since free zinc concentrations available in the human host are very low.

In 1997, Dintilhac et al {Dintilhac 1997a} concluded in their study that, besides Psa, described as an ABC-type $Mn^{2+}$ permease, and Adc, an ABC-type $Zn^{2+}$ permease, a third transporter should exist, capable of transporting both $Zn^{2+}$ and $Mn^{2+}$. The Pht proteins or the laminin-binding protein would appear as candidates to fulfill this function. Our results are indicative of a different role for the Phts. Indeed, the fact that wild-type and PhtD-deficient strains were able to grow in minimal medium in the absence of $Zn^{2+}$ and $Mn^{2+}$ is intriguing. In addition, the observation that the quadruple mutant growth was rescued with a delay when $Zn^{2+}$ or $Mn^{2+}$ was added to the minimal medium is also intriguing. These observations could be explained if we consider that the Pht proteins act as $Zn^{2+}$ and $Mn^{2+}$ scavengers, with the function to store and concentrate those divalent cations. When wild-type and PhtD-deficient mutant strains were put into minimal medium, they were able to start growing immediately thanks to the ions stored previously within the Pht proteins when bacteria were in a richer medium. In contrast, the quadruple Pht-mutants were not able to store those ions when placed in favorable conditions, and then could not grow when put in poor medium. When $Zn^{2+}$ or $Mn^{2+}$ were added in excess to minimal medium, some time was needed before the ions could be caught by the specific metal permeases, because they had to find them at random in the culture medium, without help from Pht proteins. This might explain the delay needed for the quadruple Pht mutant to start growing in such conditions. Moreover, a possible scavenging role for the Pht proteins is consistent with the presence of five to six cation-binding domains.

This speculative mechanism of storage, if confirmed, could be considered as a means for the bacterium to regulate zinc and probably manganese homeostasis. Metal ions like zinc and manganese are essential trace elements. However, they are potentially harmful to the bacterium when in excess, because they may compete with other elements as co-factors for some critical enzymes. Therefore, it is essential for the bacteria to regulate metal homeostasis, and we suggest that this is the main role of the Pht family. Such a regulatory system would allow *S. pneumoniae* to survive when facing ion-restricted environments, for example during the initial stages of the colonization process in human nasopharynx {Bunker 1984, Harlyk 1997}.

The existence of polycistronic transcripts with PhtD might be explained by the requirement of $Zn^{2+}$ or $Mn^{2+}$ for Lmb, an Lral family member, and YfnA, to exert their function. To partly support this statement, it has been suggested that $Mn^{2+}$ is required for adhesion through the Lral family of proteins, a critical feature for virulence {Dintilhac 1997b, Papp-Wallace 2006}. In addition, it has been demonstrated in other contexts that laminin binds $Zn^{2+}$ to promote high affinity binding between laminin and laminin binding proteins {Ancsin 1996, Bandyopadhyay 2002}. Therefore, we may hypothesize that Lmb needs PhtD to assure the presence of $Zn^{2+}$ when Lmb encounters laminin, which enhance binding to the host tissues. The regulation of zinc homeostasis by the Phts may also explain why these proteins have been associated with the inhibition of C3b (Hostetter, 1999 41/id; Ogunniyi, 2009 98/id). Indeed, the cleavage of C3b by factor I in the presence of factor H is regulated by zinc {Blom 2003}. By controlling zinc concentration in the bacterial environment, the Phts might thus contribute to C3b inhibition in some circumstances, which needs to be investigated further.

Therefore, by targeting the Pht protein family, the immune system may impede the possibility for the bacteria to store and use ions, which appear to be crucial for the invasion process. Consequently, our results confirm the Pht proteins as genuine vaccine candidates against pneumococcal infections. The different members of the Pht family have already been evaluated for their potential to be used as pneumococcal vaccine antigens {Adamou 2001, Hamel 2004, Ogunniyi 2007, Zhang 2001}. After their discovery, PhtA, PhtB and PhtD were examined for their ability to protect mice against a subset of pneumococcal isolates {Adamou 2001}. PhtD was found to be the Pht protein that affords the broadest protection, while PhtA immunization was efficient against a lesser number of the strains tested. This is in line with the results of the present study, where it is shown that PhtA is expressed in 62% of pneumococcal strains, while PhtD is present in 100%. Although successfully used in two studies, the potential for PhtB to elicit cross-protection is not known since it was evaluated against a single strain only {Adamou 2001, Zhang 2001}. However, since we found it in 81% of the strains, one may expect that its inter-strain coverage might not be optimal. About PhtE, this protein is found in 97% of the strains, which might be indicative of a broad cross-protection. However, this Pht shares only 32% of identity with the three other Phts, and its C-terminal part, the most immunogenic and conserved one, is PhtE-specific. The region of PhtE common with the other Phts is not accessible to antibodies {Adamou 2001, Hamel 2004}. Therefore, PhtD, present in all strains tested, with an amino-acid sequence highly conserved among pneumococci and also demonstrating cross-reactivity with PhtA and PhtB, represents a better option.

Example 7

Immunization with pht Proteins Confers Protection in a Mouse Pneumococcal Lethal Intranasal Challenge Model To evaluate the protection afforded by the members of the Pht family in a mouse pneumococcal intranasal challenge, OF1 female mice (four-weeks old; n=20/group) were immunized intramuscularly (i.m.) at day 0 and 14 with 1 μg of PhtD, PhtA, PhtB, or PhtE, formulated with the AS02 Adjuvant System that consists of an oil-in-water emulsion supplemented with 3-O-desacyl-4'-monophosphoryl lipid A (MPL) and QS21 (Garcon et al Expert Rev. Vaccines 6; 723-739 (2007). Control animals were injected with AS02 only. At day 28, the mice were challenged intranasally with the type 3/43 pneumococcal strain ($10^5$ cfu in 50 μl). Mortality was recorded for 10 days after the challenge.

In other experiments, vaccination with 1 μg of PhtD was compared with 10 μg of PspA and 10 μg of CbpA. All antigens were formulated with the Adjuvant System ASO4, consisting of aluminum salts with MPL (Garcon et al Expert Rev. Vaccines 6; 723-739 (2007). The i.m. immunizations occurred at day 0, 14 and 28. Control animals were vaccinated with adjuvant only. At day 42, the mice were challenged intranasally with *S. pneumoniae* type 4/CDC ($5\times10^6$ cfu), type 2/D39 ($2\times10^5$ cfu), or type 3/43 ($10^5$ cfu) in 50 μl. The mortality was recorded for 10 days after the challenge. Survival data were analyzed with the logrank test (Mantel-Haenszel).

The results indicate that vaccination with either of the Pht proteins allowed the survival of approximately 60% of mice, while only 20% of the animals survived in the control group (FIG. 1).

In subsequent experiments, other groups of animals were vaccinated with three different pneumococcal antigens, PspA, CbpA, and one protein of the Pht family, namely PhtD. The extent of the humoral response was evaluated and the animals were challenged with three different pneumococcal strains two weeks after the last immunization. Mice survival was recorded for all antigen/strain combinations.

The resulting levels of antibodies were antigen-dependent (FIG. 2A). Vaccination with 1 µg of PhtD elicited higher antibody titers than vaccination with 10 µg of CbpA or PspA. Nevertheless, the level of protection against intra-nasal lethal challenge with the 2/D39 strain, from which CbpA and PspA originate, was similar for the three antigens, with around 70% of survival (FIG. 3A). Differences between the antigens were evidenced when other strains were used. Indeed, vaccination with PhtD allowed 60% and 80% of mice to survive the challenge with the 3/43 and the 4/CDC strains, respectively. In contrast, CbpA and PspA afforded no or very weak protection against the type-3 and -4 challenges. PhtD was thus the only antigen able to afford protection against the three strains.

Example 8

Immunization with Pht Proteins Protects Mice Against S. pneumoniae Nasopharyngeal Colonization A nasopharyngeal colonisation assay was used to assess the ability of immunization against PhtD to prevent otitis media. Several studies have shown a link between nasopharylgeal colonisation and otitis media. Bogaert et al Lancet Infect. Dis. 4(3); 144-154 (2004) showed that colonisation rates tend to be higher during respiratory tract infection and otitis media. Indeed pneumococcal disease will not occur without proceeding and/or concurrent nasopharyngeal colonisation with the homologous strain (Grey et al J. Infect. Dis. 142; 923-933 (1980), Syrjanea et al Paediatr. Infect. Dis. J. 24; 801-806 (2005)).

Balb/c mice (four-weeks old; n=10/group) were immunized at days 0, 14 and 28 by the intranasal route with 5 µg of PhtD, PhtA, PhtB, or PhtE supplemented with 0.2 µg of E. coli labile toxin (LT) as an adjuvant (except in the last immunization). Another experiment with the same protocol (schedule and dosages) consisted in comparing PhtD with CbpA, PsaA, and PspA. Control mice were injected with LT alone. At day 42, mice were challenged intranasally with $7 \times 10^4$ cfu of type 6B/CDC strain, type 4/CDC, or type 2/D39. The challenges were performed using a small bacterial inoculum volume (10 µl). Bacterial colonies were counted in nasal washings collected 2 and 6 days after the challenge. Nasal washings were obtained by flushing 500 µl of PBS inside the nasal cavity of anaesthetized mice. Next, to count the bacterial colonies, 100 µl of nasal washing was diluted ten times in Todd Hewitt Broth. From this, 10 µl was plated onto Difco™ Blood Agar base supplemented with definibrated, sterile sheep blood and gentamycin (3 µg/ml). The Petri dish was tilted to spread the sample and the colonies were enumerated after incubation overnight at 37° C. All colony countings data, after normalization, were compared with ANOVA, followed by the Dunnett post-test when ANOVA was found significant.

To assess the protective activity of vaccination against naso-pharyngeal carriage, Balb/c mice were immunized intranasally with the different Pht proteins before they were challenged via the same route with the 2/D39 strain. As can be seen in FIG. 4, although only vaccination with PhtD or PhtE afforded significant protection against the challenge with the type 2 strain, all members of the Pht family were able to reduce bacterial load in the nasopharynx of the vaccinated animals. Due to the better performance of PhtD in this model, this member of the Pht family was chosen for further experiments, consisting in comparing PhtD with other pneumococcal proteins. Therefore, mice were immunized with different pneumococcal antigens, including PhtD, and were subsequently challenged with a type 2, a type 4 or a type 6B strain.

As was observed after systemic immunization, the elicited humoral responses after intra-nasal immunization were antigen-dependent (FIG. 2B). Particularly, CbpA elicited lower antibody titers than PspA and PhtD. However, the level of protection afforded by CbpA against the Glade-homologous 2/D39 strain was similar to that of PspA and PhtD (FIG. 5A). When the type4/CDC was used for the challenge, only immunization with PhtD could protect the animals against naso-pharyngeal colonization, whereas immunization with CbpA, PsaA or PspA was not statistically distinguishable from the LT control (FIG. 5B). Finally, challenge with type 6B/CDC did not evidence any difference in protection at day 2 post-challenge whether the animals were immunized with CbpA, PspA or PhtD (FIG. 5C). Only PsaA seemed to be less efficient in that respect. At day 6 post-challenge, there was no statistical difference between all groups. However, a careful examination of the results for PhtD revealed that the majority of animals were protected against naso-pharyngeal colonization and that the unfavorable statistical conclusion was probably only due to the presence of two outliers. In conclusion, PhtD was the only antigen able to afford some protection against the three strains in this model of naso-pharyngeal colonization.

Example 9

Immunization with PhtD Protects Mice Against S. pneumoniae Lung Colonization

The model was adapted from Briles et al J. Infect. Dis. 188; 339-348 (2003). CBA/J female mice (four-weeks old; 30/group) were immunized i.m. at day 0, 14 and 28 with 3 µg of PhtD adjuvanted with AS02. At day 42, the mice were challenged intranasally with $2 \times 10^7$ cfu/50 µl of S. pneumoniae 19F/2737. Control mice were injected with adjuvant only. Bacterial load was measured by colony counting in lungs collected 3, 4 and 5 days post-challenge. All colony countings data, after normalization, were compared with ANOVA, followed by the Dunnett post-test when ANOVA was found significant.

CBA/J mice, a strain susceptible to pneumococcal infections, were vaccinated with PhtD before they were challenged with a moderately virulent 19F bacterial strain. Such a protocol allows for the induction of a focal pneumonia without generalized sepsis. After the challenge, the number of living bacteria in the lungs was evaluated at day 3, 4 and 5.

It was shown that vaccination with PhtD reduced the bacterial load in the lungs to a great extent (more than 95%), as compared with placebo (FIG. 6a). The efficacy of PhtD vaccination was particularly evident when analyzing the number of non-colonized mice, since up to 80% of vaccinated mice remained free of bacteria at day 5, as compared with 10% in the control group (FIG. 6b).

REFERENCES

1 Adamou J E, Heinrichs J H, Erwin A L, et al. Identification and characterization of a novel family of pneumococcal proteins that are protective against sepsis. *Infect. Immun.* 69(2), 949-958 (2001).

2 Ajdic D, McShan W M, McLaughlin R E, et al. Genome sequence of *Streptococcus mutans* UA159, a cariogenic dental pathogen. *Proc. Natl. Acad. Sci. U. S. A* 99(22), 14434-14439 (2002).

3 Ancsin J B, Kisilevsky R. Laminin interactions important for basement membrane assembly are promoted by zinc and implicate laminin zinc finger-like sequences. *J. Biol. Chem.* 271(12), 6845-6851 (1996).

4 Bandyopadhyay K, Karmakar S, Ghosh A, Das P K. High affinity binding between laminin and laminin binding protein of *Leishmania* is stimulated by zinc and may involve laminin zinc-finger like sequences. *Eur. J. Biochem.* 269(6), 1622-1629 (2002).

5 Beghetto E, Gargano N, Ricci S, et al. Discovery of novel *Streptococcus pneumoniae* antigens by screening a whole-genome λ-display library. *FEMS Microbiol. Lett.* 262(1), 14-21 (2006).

6 Blom A M, Kask L, Ramesh B, Hillarp A. Effects of zinc on factor I cofactor activity of C4b-binding protein and factor H. *Arch. Biochem. Biophys.* 418(2), 108-118 (2003).

7 Brendel V, Trifonov E N. A computer algorithm for testing potential prokaryotic terminators. *Nucleic Acids Res.* 12(10), 4411-4427 (1984).

8 Brenot A, Weston B F, Caparon M G. A PerR-regulated metal transporter (PmtA) is an interface between oxidative stress and metal homeostasis in *Streptococcus pyogenes*. *Mol. Microbiol.* 63(4), 1185-1196 (2007).

9 Bridy-Pappas A E, Margolis M B, Center K J, Isaacman D J. *Streptococcus pneumoniae*: description of the pathogen, disease epidemiology, treatment, and prevention. *Pharmacotherapy* 25(9), 1193-1212 (2005).

10 Bunker V W, Hinks L J, Lawson M S, Clayton B E. Assessment of zinc and copper status of healthy elderly people using metabolic balance studies and measurement of leucocyte concentrations. *Am. J. Clin. Nutr.* 40(5), 1096-1102 (1984).

11 Claverys J-P. A new family of high-affinity ABC manganese and zinc permeases. *Res. Microbiol.* 152(3-4), 231-243 (2001).

12 Cockayne A, Hill P J, Powell N B L, Bishop K, Sims C, Williams P. Molecular cloning of a 32-kilodalton lipoprotein component of a novel iron-regulated *Staphylococcus epidermidis* ABC transporter. *Infect. Immun.* 66(8), 3767-3774 (1998).

13 Dagan R, Engelhard D, Piccard E, Englehard D. Epidemiology of invasive childhood pneumococcal infections in Israel. The Israeli Pediatric Bacteremia and Meningitis Group. *JAMA* 268(23), 3328-3332 (1992).

14 Dagan R, Käyhty H, Wuorimaa T, et al. Tolerability and immunogenicity of an eleven valent mixed carrier *Streptococcus pneumoniae* capsular polysaccharide-diphtheria toxoid or tetanus protein conjugate vaccine in Finnish and Israeli infants. *Pediatr. Infect. Dis. J.* 23(2), 91-98 (2004).

15 Dintilhac A, Alloing G, Granadel C, Claverys J-P. Competence and virulence of *Streptococcus pneumoniae*: Adc and PsaA mutants exhibit a requirement for Zn and Mn resulting from inactivation of putative ABC metal permeases. *Mol. Microbiol.* 25(4), 727-739 (1997a).

16 Dintilhac A, Claverys J-P. The adc locus, which affects competence for genetic transformation in *Streptococcus pneumoniae*, encodes an ABC transporter with a putative lipoprotein homologous to a family of streptococcal adhesins. *Res. Microbiol.* 148(2), 119-131 (1997b).

17 Elsner A, Kreikemeyer B, Braun-Kiewnick A, Spellerberg B, Buttaro B A, Podbielski A. Involvement of Lsp, a member of the Lral-lipoprotein family in *Streptococcus pyogenes*, in eukaryotic cell adhesion and internalization. *Infect. Immun.* 70(9), 4859-4869 (2002).

18 Fedson D C and Musher D M. Pneumococcal polysaccharide vaccines. In: Vaccines, edited by Plotkin S A and Orenstein W A, Philadelphia, Pa.:Elsevier, Inc, 2004, p. 529-588.

19 Ferretti J J, McShan W M, Ajdic D, et al. Complete genome sequence of an M1 strain of *Streptococcus pyogenes*. *Proc. Natl. Acad. Sci. U. S. A* 98(8), 4658-4663 (2001).

20 Gagnon G, Vadeboncoeur C, Levesque R C, Frenette M. Cloning, sequencing and expression in *Escherichia coli* of the ptsI gene encoding enzyme I of the phosphoenolpyruvate:sugar phosphotransferase transport system from *Streptococcus salivarius*. *Gene* 121(1), 71-78 (1992).

21 Hamel J, Charland N, Pineau I, et al. Prevention of pneumococcal disease in mice immunized with conserved surface-accessible proteins. *Infect. Immun.* 72(5), 2659-2670 (2004).

22 Hanahan D. Plasmid transformation by Simanis. In: DNA cloning, edited by Glover D M, London:IRL Press, 1985, p. 109-135.

23 Harlyk C, Mccourt J, Bordin G, Rodriguez A R, van der Eeckhout A. Determination of copper, zinc and iron in broncho-alveolar lavages by atomic absorption spectroscopy. *J. Trace Elem. Med. Biol.* 11(3), 137-142 (1997).

24 Hausdorff W P, Feikin D R, Klugman K P. Epidemiological differences among pneumococcal serotypes. *Lancet Infect. Dis.* 5(2), 83-93 (2005).

25 Hava D L, Camilli A. Large-scale identification of serotype 4 *Streptococcus pneumoniae* virulence factors. *Mol. Microbiol.* 45(5), 1389-1405 (2002).

26 Hoskins J, Alborn W E, Jr., Arnold J, et al. Genome of the bacterium *Streptococcus pneumoniae* strain R6. *J. Bacteriol.* 183(19), 5709-5717 (2001).

27 Hostetter M K. Opsonic and nonopsonic interactions of C3 with *Streptococcus pneumoniae*. *Microb. Drug Resist.* 5(2), 85-89 (1999).

28 Jenkinson H F. Cell surface protein receptors in oral streptococci. *FEMS Microbiol. Lett.* 121(2), 133-140 (1994).

29 Kunst F, Ogasawara N, Moszer I, et al. The complete genome sequence of the gram-positive bacterium *Bacillus subtilis*. *Nature* 390(6657), 249-256 (1997).

30 Laemmli U K. Cleavage of structural proteins during the assembly of the head of bacteriophage T4. *Nature* 227(5259), 680-685 (1970).

31 Loisel E, Jacquamet L, Serre L, et al. AdcAII, a new pneumococcal Zn-binding protein homologous with ABC transporters: biochemical and structural analysis. *J. Mol. Biol.* 381(3), 594-606 (2008).

32 Lynch J P, Ill, Zhanel G G. Escalation of antimicrobial resistance among *Streptococcus pneumoniae*: implications for therapy. *Semin. Respir. Crit Care Med.* 26(6), 575-616 (2005).

33 Mbelle N, Huebner R E, Wasas A D, Kimura A, Chang I, Klugman K P. Immunogenicity and impact on nasopharyngeal carriage of a nonavalent pneumococcal conjugate vaccine. *J. Infect. Dis.* 180(4), 1171-1176 (1999).

34 McCullers J A, Tuomanen EI. Molecular pathogenesis of pneumococcal pneumonia. *Front Biosci.* 6, D877-D889 (2001).

35 Morrison D A, Jaurin B. *Streptococcus pneumoniae* possesses canonical *Escherichia coli* (sigma 70) promoters. *Mol. Microbiol.* 4(7), 1143-1152 (1990).

36 Nunes S, Sá-Leão R, Pereira L C, de Lencastre H. Emergence of a serotype 1 *Streptococcus pneumoniae* lineage 36. colonising healthy children in Portugal in the seven-valent conjugate vaccination era. *Clin. Microbiol. Infect.* 14(1), 82-84 (2008).
37. Ogunniyi A D, Grabowicz M, Briles D E, Cook J, Paton J C. Development of a vaccine against invasive pneumococcal disease based on combinations of virulence proteins of *Streptococcus pneumoniae*. *Infect. Immun.* 75(1), 350-357 (2007).
38. Ogunniyi A D, Grabowicz M, Mandi L K, et al. Pneumococcal histidine triad proteins are regulated by the Zn2+-dependent repressor AdcR and inhibit complement deposition through the recruitment of complement factor H. *FASEB J.* 23(3), 731-738 (2009).
39. Panina E M, Mironov A A, Gelfand M S. Comparative genomics of bacterial zinc regulons: enhanced ion transport, pathogenesis, and rearrangement of ribosomal proteins. *Proc. Natl. Acad. Sci. U. S. A* 100(17), 9912-9917 (2003).
40. Papp-Wallace K M, Maguire M E. Manganese transport and the role of manganese in virulence. *Annu. Rev. Microbiol.* 60, 187-209 (2006).
41. Peterson J D, Umayam L A, Dickinson T, Hickey E K, White O. The Comprehensive Microbial Resource. *Nucleic Acids Res.* 29(1), 123-125 (2001).
42. Ranasinghe C, Hobbs A A. A simple method to obtain the 5' ends of mRNA sequences by direct ligation of cDNA-RNA hybrids to a plasmid vector. *Technical Tips Online* 3(1), 128-132 (1998).
43. Riboldi-Tunnicliffe A, Isaacs N W, Mitchell T J. 1.2 Å crystal structure of the *S. pneumoniae* PhtA histidine triad domain a novel zinc binding fold. *FEBS Lett.* 579(24), 5353-5360 (2005).
44. Rosenberg M, Court D. Regulatory sequences involved in the promotion and termination of RNA transcription. *Annu. Rev. Genet.* 13, 319-353 (1979).
45. SICARD A M. A new synthetic medium for *Diplococcus pneumoniae*, and its use for the study of reciprocal transformation at the amiA locus. *Genetics* 50, 31-44 (1964).
46. Singleton R J, Hennessy T W, Bulkow L R, et al. Invasive pneumococcal disease caused by nonvaccine serotypes among alaska native children with high levels of 7-valent pneumococcal conjugate vaccine coverage. *JAMA* 297(16), 1784-1792 (2007).
47. Smart L E, Dougall A J, Girdwood R W A. New 23-valent pneumococcal vaccine in relation to pneumococcal serotypes in systemic and non-systemic disease. *J. Infect.* 14(3), 209-215 (1987).
48. Spellerberg B, Rozdzinski E, Martin S, et al. Lmb, a protein with similarities to the Lral adhesin family, mediates attachment of *Streptococcus agalactiae* to human laminin. *Infect. Immun.* 67(2), 871-878 (1999).
49. Tettelin H, Nelson K E, Paulsen I T, et al. Complete genome sequence of a virulent isolate of *Streptococcus pneumoniae*. *Science* 293(5529), 498-506 (2001).
50. Towbin H, Staehelin T, Gordon J. Electrophoretic transfer of proteins from polyacrylamide gels to nitrocellulose sheets: procedure and some applications. *Proc. Natl. Acad. Sci. U. S. A* 76(9), 4350-4354 (1979).
51. Turner D H, Sugimoto N, Freier S M. RNA structure prediction. *Annu. Rev. Biophys. Biophys. Chem.* 17, 167-192 (1988).
52. Wizemann™, Heinrichs J H, Adamou J E, et al. Use of a whole genome approach to identify vaccine molecules affording protection against *Streptococcus pneumoniae* infection. *Infect. Immun.* 69(3), 1593-1598 (2001).
53. Yamamoto H, Uchiyama S, Nugroho F A, Sekiguchi J. A 23.4 kb segment at the 69°-70° region of the *Bacillus subtilis* genome. *Microbiology* 143 (Pt 4), 1317-1320 (1997).
54. Zhang Y, Masi A W, Barniak V, Mountzouros K, Hostetter M K, Green B A. Recombinant PhpA protein, a unique histidine motif-containing protein from *Streptococcus pneumoniae*, protects mice against intranasal pneumococcal challenge. *Infect. Immun.* 69(6), 3827-3836 (2001).

The invention claimed is:

1. A method of treating a *Streptococcus pneumoniae* infection in a mammal comprising:
   (a) measuring the amount of bound and free Zn2+ in the blood serum of a mammal;
   (b) selecting a mammal having a bound and free Zn2+ concentration in blood serum of less than 2 μM; and
   (b) administering an immunogenic composition comprising a pharmaceutically effective amount of PhtD to the mammal selected in step (b).

2. The method of claim 1 wherein the immunogenic composition is administered intramuscularly.

3. The method of claim 1 where in the immunogenic composition further comprises an adjuvant.

* * * * *

SEQUENCE LISTING

```
<160> NUMBER OF SEQ ID NOS: 19

<210> SEQ ID NO 1
<211> LENGTH: 180
<212> TYPE: DNA
<213> ORGANISM: S.pneumoniae

<400> SEQUENCE: 1
tcttttttag aaaaacgtaa cagaaacttg acaaaagtaa ttttaaatag taaactattt      60
actggttaat taaatggtta aataaccggt ttagaaaact atttaataaa gtaaaagaag     120
ttgagaaaaa acttcatcat ttattgaaat gagggattta tgaaatttag taaaaaatat     180

<210> SEQ ID NO 2
<211> LENGTH: 170
<212> TYPE: DNA
<213> ORGANISM: S.pneumoniae

<400> SEQUENCE: 2
aaaattcttg acaagttgga tatttaggag taaactatta accagttaag taatagagag      60
gagtttctgc aatttagaaa tgaattgcaa ctagaaatat caaatagaaa gagagtttcg     120
atgaaaatta ataagaaata ccttgttggt tctgcggcag ctttgatttt                170

<210> SEQ ID NO 3
```

```
<211> LENGTH: 120
<212> TYPE: DNA
<213> ORGANISM: S.pneumoniae

<400> SEQUENCE: 3
ttcttgacaa gcaatattaa aaagagtaaa ctattaacta gttaattaac cggtttatta      60
ctttatagtg aatcaaatat acttaagaaa agaggaaaga atgaaaatta ataaaaaata    120

<210> SEQ ID NO 4
<211> LENGTH: 108
<212> TYPE: DNA
<213> ORGANISM: S.pneumoniae

<400> SEQUENCE: 4
ctaaaaatat cttgacagat taaattttca ggagtagaat atttactagt taattaaagg      60
ttaaggagtt gttcatgaag aaacaaaatt tatttttagt cctgttaa                 108

<210> SEQ ID NO 5
<211> LENGTH: 120
<212> TYPE: DNA
<213> ORGANISM: S.pneumoniae

<400> SEQUENCE: 5
gttacggtag tcagattttt ttagaaaaac attttataaa tattcacata tctcctatat      60
ttatggtaaa atagaattat cagtttattt tggagtcaaa gatgaatata tttagaacaa    120

<210> SEQ ID NO 6
<211> LENGTH: 30
<212> TYPE: DNA
<213> ORGANISM: S.pneumoniae

<400> SEQUENCE: 6
atctgatctc atagcgtaag gaatagcagt                                      30

<210> SEQ ID NO 7
<211> LENGTH: 180
<212> TYPE: DNA
<213> ORGANISM: S.pneumoniae

<400> SEQUENCE: 7
aattatgaaa tttaaaaaga aatatatagc agctggatct gttgttatcc tttccttaag      60
tctgtgtgtt tatgctctga accaacatag ctaacaggcc aatacagata aaaatcgtgt    120
ttcatatgta aacagtaata aagacactaa gaagactgaa aatttgactc cagactaggt    180

<210> SEQ ID NO 8
<211> LENGTH: 131
<212> TYPE: DNA
<213> ORGANISM: S.pneumoniae

<400> SEQUENCE: 8
tcagttaggt taagggagga tatattatta aggtagatgg aaagtattat gtttacctta      60
aagatcaagc tcatgcagaa aatgtacgaa caaaagatga atcaatcgc caaaaacaag    120 aacatggtaa a                                                         131

<210> SEQ ID NO 9
<211> LENGTH: 70
<212> TYPE: DNA
<213> ORGANISM: S.pneumoniae

<400> SEQUENCE: 9
```

-continued

```
tagcgccctt caacaagaaa aggaaaatgc tgagcaagat cctcagacac ttgtactcta    60
tcaaaaactc                                                            70
```

<210> SEQ ID NO 10
<211> LENGTH: 133
<212> TYPE: DNA
<213> ORGANISM: S.pneumoniae

<400> SEQUENCE: 10

```
aaactattgg ctttattaaa ggagagtaag taaaggtagc agcatttttct aactcctaaa   60 acaggatagg agaacgggaa acgaaaaat gagagcagaa tgtgagttct agttctcatt   120
tttttcatga aat                                                      133
```

<210> SEQ ID NO 11
<211> LENGTH: 113
<212> TYPE: DNA
<213> ORGANISM: S.pneumoniae

<400> SEQUENCE: 11

```
aaagaaagtc aaccggctcc tatacagtag taaaatgaat ggagcatatt ttatggagaa   60
gtaacctttc gtgttacttc tcttttttag aaaaacgtaa cagaaacttg aca           113
```

<210> SEQ ID NO 12
<211> LENGTH: 104
<212> TYPE: DNA
<213> ORGANISM: S.pneumoniae

<400> SEQUENCE: 12

```
agtaaggaaa aaataaacta atgaaaaatg aaagtctcga taaagaggct ttcattttta   60
ttatgtatat atgtaaaatt cttgacaagc aatattaaaa agag                     104
```

<210> SEQ ID NO 13
<211> LENGTH: 66
<212> TYPE: DNA
<213> ORGANISM: S.pneumoniae

<400> SEQUENCE: 13

```
acgttaattt tgattaatcg aaaagtccct gcaactcagt tacagggatt ttttgatat    60 tttaaa                                                               66
```

<210> SEQ ID NO 14
<211> LENGTH: 19
<212> TYPE: PRT
<213> ORGANISM: S.pneumoniae

<400> SEQUENCE: 14

```
Met Lys Ile Asn Lys Lys Tyr Leu Val Gly Ser Ala Ala Ala Leu Ile
1               5                   10                  15

Leu Ser Val
```

<210> SEQ ID NO 15
<211> LENGTH: 19
<212> TYPE: PRT
<213> ORGANISM: S.pneumoniae

<400> SEQUENCE: 15

```
Met Lys Ile Asn Lys Lys Tyr Leu Ala Gly Ser Val Ala Thr Leu Val
1               5                   10                  15
```

```
<210> SEQ ID NO 16
<211> LENGTH: 19
<212> TYPE: PRT
<213> ORGANISM: S.pneumoniae

<400> SEQUENCE: 16

Met Lys Ile Asn Lys Lys Tyr Leu Ala Gly Ser Val Ala Val Leu Val
1               5                   10                  15
Leu Ser Val

<210> SEQ ID NO 17
<211> LENGTH: 19
<212> TYPE: PRT
<213> ORGANISM: S.pneumoniae

<400> SEQUENCE: 17

Met Lys Ile Asn Lys Lys Tyr Leu Ala Gly Ser Val Ala Val Leu Ala
1               5                   10                  15
Leu Ser Val

<210> SEQ ID NO 18
<211> LENGTH: 19
<212> TYPE: PRT
<213> ORGANISM: S.pneumoniae

<400> SEQUENCE: 18

Met Lys Ile Asn Lys Lys Tyr Val Ala Gly Ser Val Ala Val Leu Ala
1               5                   10                  15
Leu Ser Val

<210> SEQ ID NO 19
<211> LENGTH: 20
<212> TYPE: PRT
<213> ORGANISM: S.pneumoniae

<400> SEQUENCE: 19

Met Lys Phe Ser Lys Lys Tyr Ile Ala Ala Gly Ser Ala Val Ile Val
1               5                   10                  15
Ser Leu Ser Leu
                20
```